(12) United States Patent (10) Patent No.: US 12,658,305 B2
Ito (45) Date of Patent: Jun. 16, 2026

(54) MEDICAL SUPPORT DEVICE, AND OPERATION METHOD AND OPERATION PROGRAM OF MEDICAL SUPPORT DEVICE

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 369 days.

(21) Appl. No.: 18/186,205

(22) Filed: Mar. 20, 2023

(65) Prior Publication Data

US 2023/0317249 A1 Oct. 5, 2023

(30) Foreign Application Priority Data

Mar. 31, 2022 (JP) ................................. 2022-060859

(51) Int. Cl.
*G16H 50/20* (2018.01)
*G06T 7/11* (2017.01)
*G16H 30/20* (2018.01)
*G16H 30/40* (2018.01)
*G06T 7/00* (2017.01)

(52) U.S. Cl.
CPC .............. *G16H 30/20* (2018.01); *G06T 7/11* (2017.01); *G16H 30/40* (2018.01); *G06T 7/0012* (2013.01)

(58) Field of Classification Search
USPC ........................ 128/915–916, 920, 922–925; 382/128–133, 154–159, 173–225; 706/1–62, 900–903
See application file for complete search history.

(56) References Cited

U.S. PATENT DOCUMENTS

| | | | | |
|---|---|---|---|---|
| 6,058,322 A * | 5/2000 | Nishikawa | ............ | G06T 7/0012 |
| | | | | 382/128 |
| 12,437,391 B2 | 10/2025 | Nielsen et al. | | |
| 2018/0024995 A1 | 1/2018 | Choi et al. | | |
| 2020/0202532 A1 | 6/2020 | Wang et al. | | |
| 2023/0351586 A1* | 11/2023 | Brynolfsson | ............ | G06T 7/11 |

FOREIGN PATENT DOCUMENTS

| | | |
|---|---|---|
| JP | 2016073542 | 5/2001 |
| JP | 2002112985 | 4/2002 |
| JP | 2004248818 | 9/2004 |
| JP | 2005118510 | 5/2005 |
| JP | 2005131010 | 5/2005 |
| JP | 2005131011 | 5/2005 |

(Continued)

OTHER PUBLICATIONS

Mizobe Hidekane; Diagnosis Support Device, Diagnosis Support System, Information Processing Method, and Program; 2020 (Year: 2020).*

(Continued)

*Primary Examiner* — Marcellus J Augustin
(74) *Attorney, Agent, or Firm* — JCIPRNET

(57) ABSTRACT

A processor of a medical support device is configured to execute first display control for displaying abnormal signal regions detected by performing image analysis on a medical image, in an identifiable manner and second display control for changing a display aspect for each group classified by an operation instruction, on the abnormal signal regions.

12 Claims, 18 Drawing Sheets

(56) References Cited

FOREIGN PATENT DOCUMENTS

| JP | 2019213785 | 12/2019 |
| WO | 2012032940 | 3/2012 |
| WO | 2020260671 | 12/2020 |
| WO | 2023145953 | 8/2023 |

OTHER PUBLICATIONS

Taguchi Katsuyuki; Medical Information Processing System For Supporting Diagnosis; 2000 (Year: 2000).*
"Notice of Reasons for Refusal of Japan Counterpart Application", issued on Dec. 2, 2025, with English translation thereof, p. 1-p. 8.

* cited by examiner

SETTING INFORMATION

~50A

SECOND LIST
SETTING
INFORMATION

|  | H/L | GROUP NAME | DISPLAY ASPECT |
|---|---|---|---|
| 1 | H | SUBARACHNOIDAL BLEEDING | P1 |
| 2 | H | INTRACEREBRAL BLEEDING | P2 |
| 3 | H | LVO | P3 |
| 4 | H | Hyperdense Sign | P4 |
| 5 | H | CALCIFICATION | P5 |
| ⋮ | ⋮ | ⋮ | ⋮ |
| 11 | L | INFARCTION | P11 |
| ⋮ | ⋮ | ⋮ | ⋮ |

FIG. 13
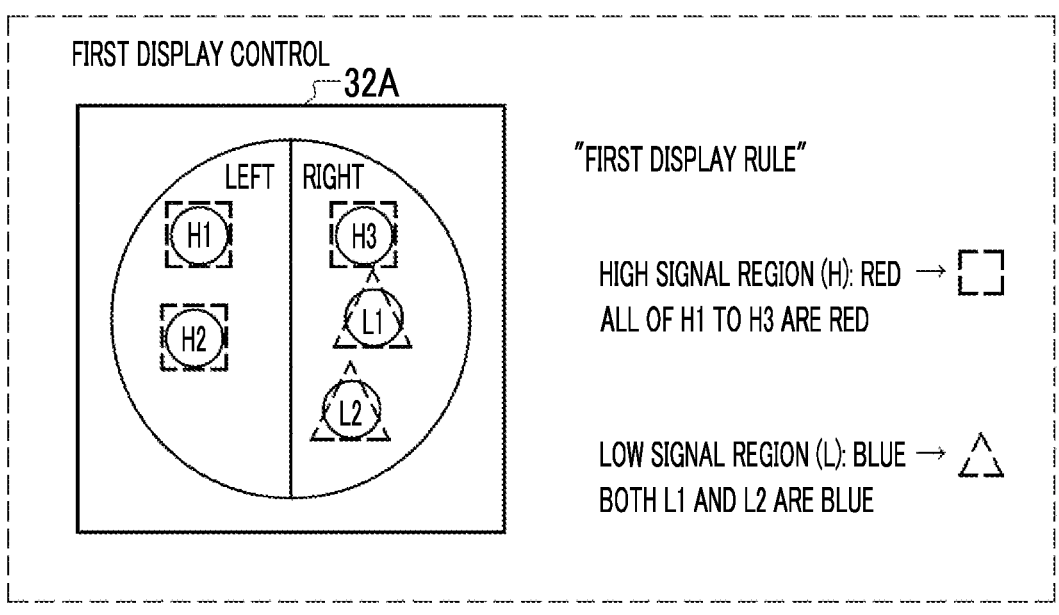
FIRST DISPLAY CONTROL
32A
LEFT | RIGHT
"FIRST DISPLAY RULE"
HIGH SIGNAL REGION (H): RED →
ALL OF H1 TO H3 ARE RED
LOW SIGNAL REGION (L): BLUE →
BOTH L1 AND L2 ARE BLUE
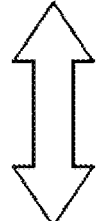
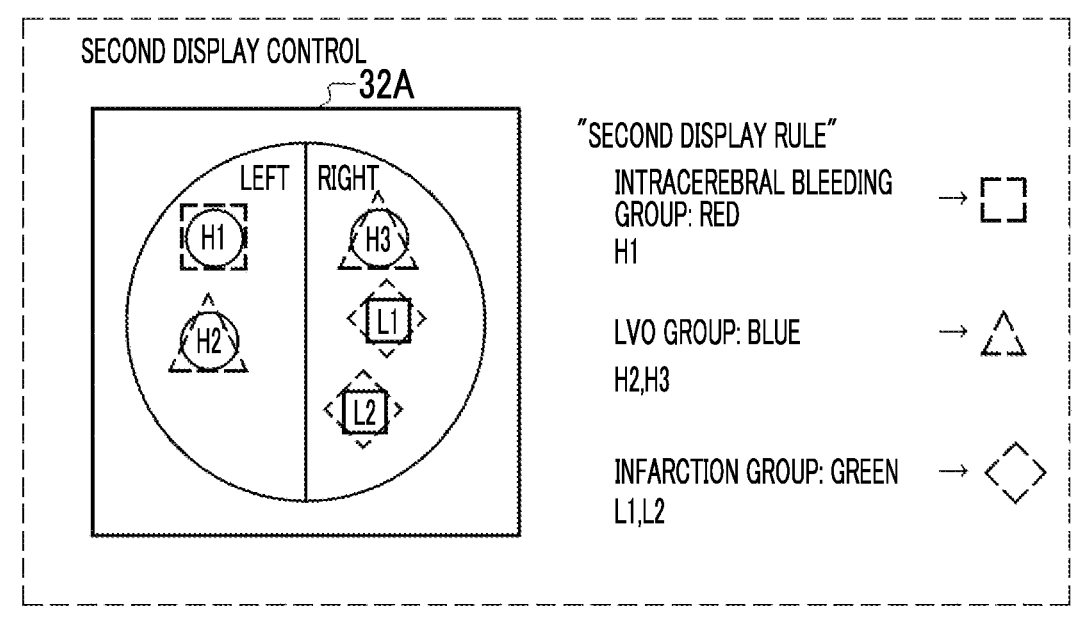
SECOND DISPLAY CONTROL
32A
LEFT | RIGHT
"SECOND DISPLAY RULE"
INTRACEREBRAL BLEEDING
GROUP: RED →
H1
LVO GROUP: BLUE →
H2,H3
INFARCTION GROUP: GREEN →
L1,L2

FIG. 15

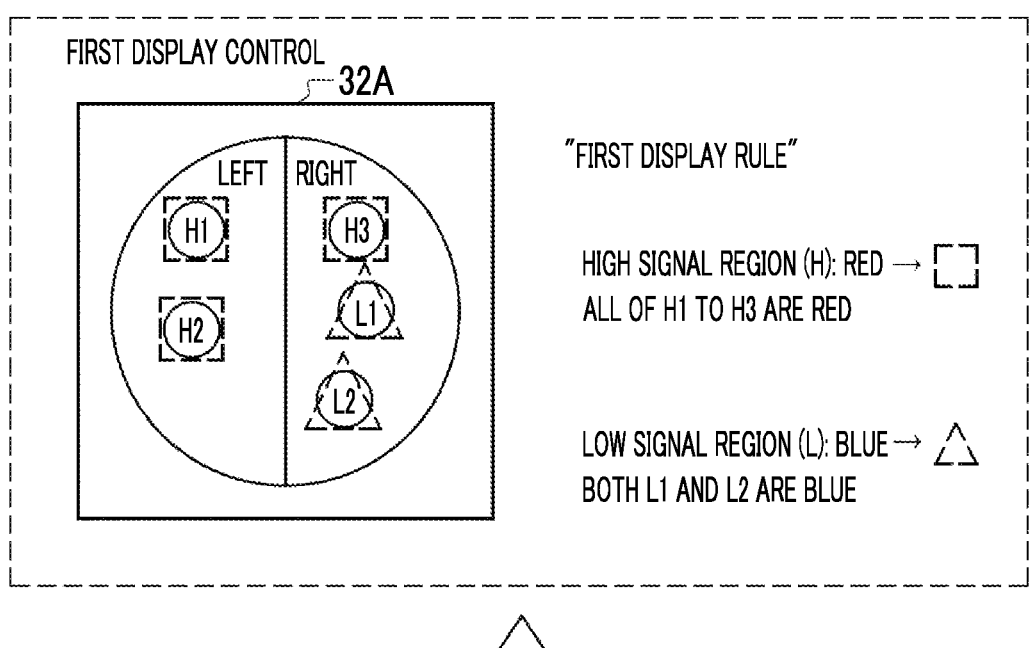

FIRST DISPLAY CONTROL
~32A

"FIRST DISPLAY RULE"

HIGH SIGNAL REGION (H): RED →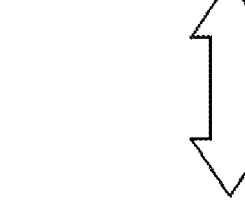
ALL OF H1 TO H3 ARE RED

LOW SIGNAL REGION (L): BLUE → △
BOTH L1 AND L2 ARE BLUE

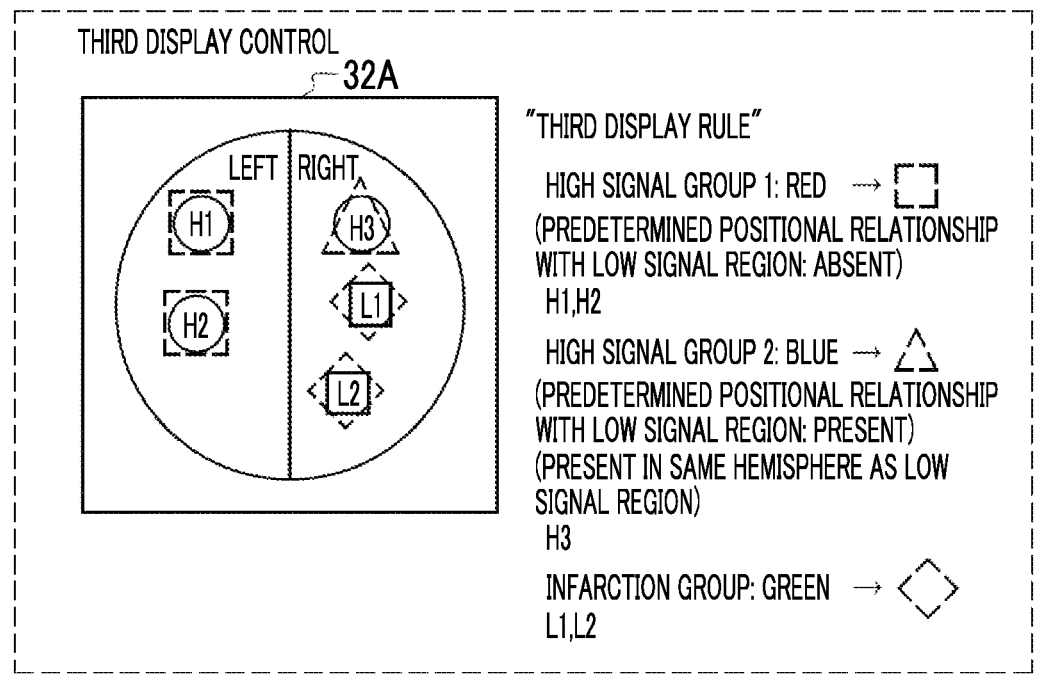

THIRD DISPLAY CONTROL
~32A

"THIRD DISPLAY RULE"

HIGH SIGNAL GROUP 1: RED → ☐
(PREDETERMINED POSITIONAL RELATIONSHIP
WITH LOW SIGNAL REGION: ABSENT)
H1,H2

HIGH SIGNAL GROUP 2: BLUE → △
(PREDETERMINED POSITIONAL RELATIONSHIP
WITH LOW SIGNAL REGION: PRESENT)
(PRESENT IN SAME HEMISPHERE AS LOW
SIGNAL REGION)
H3

INFARCTION GROUP: GREEN → ◇
L1,L2

FIG. 17

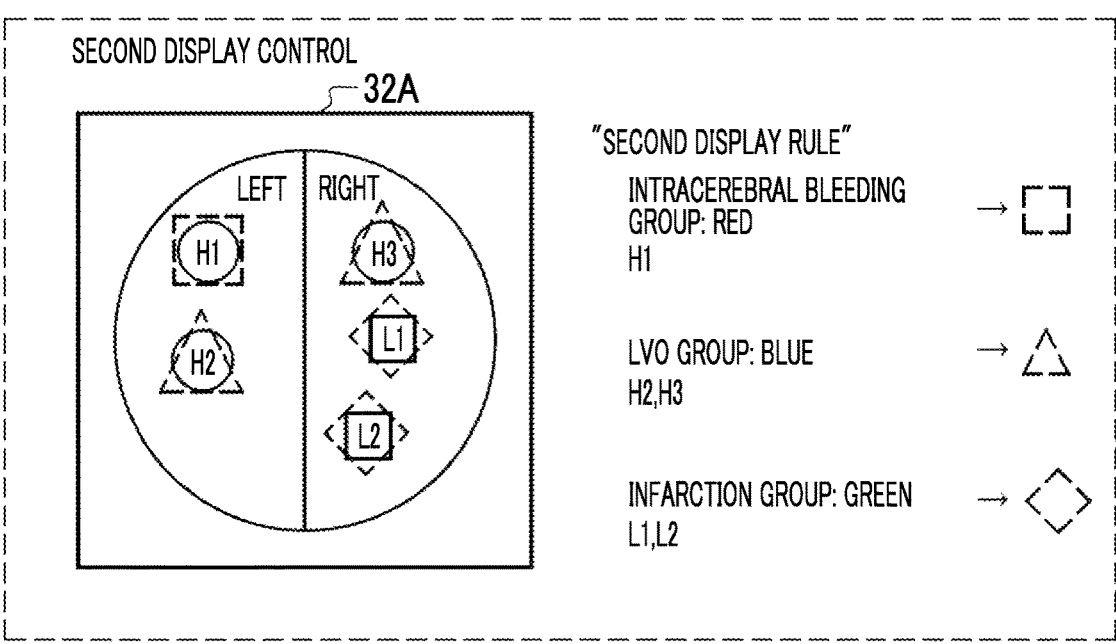

SECOND DISPLAY CONTROL

"SECOND DISPLAY RULE"

INTRACEREBRAL BLEEDING
GROUP: RED          →  ☐
H1

LVO GROUP: BLUE          →  △
H2,H3

INFARCTION GROUP: GREEN          →  ◇
L1,L2

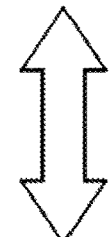

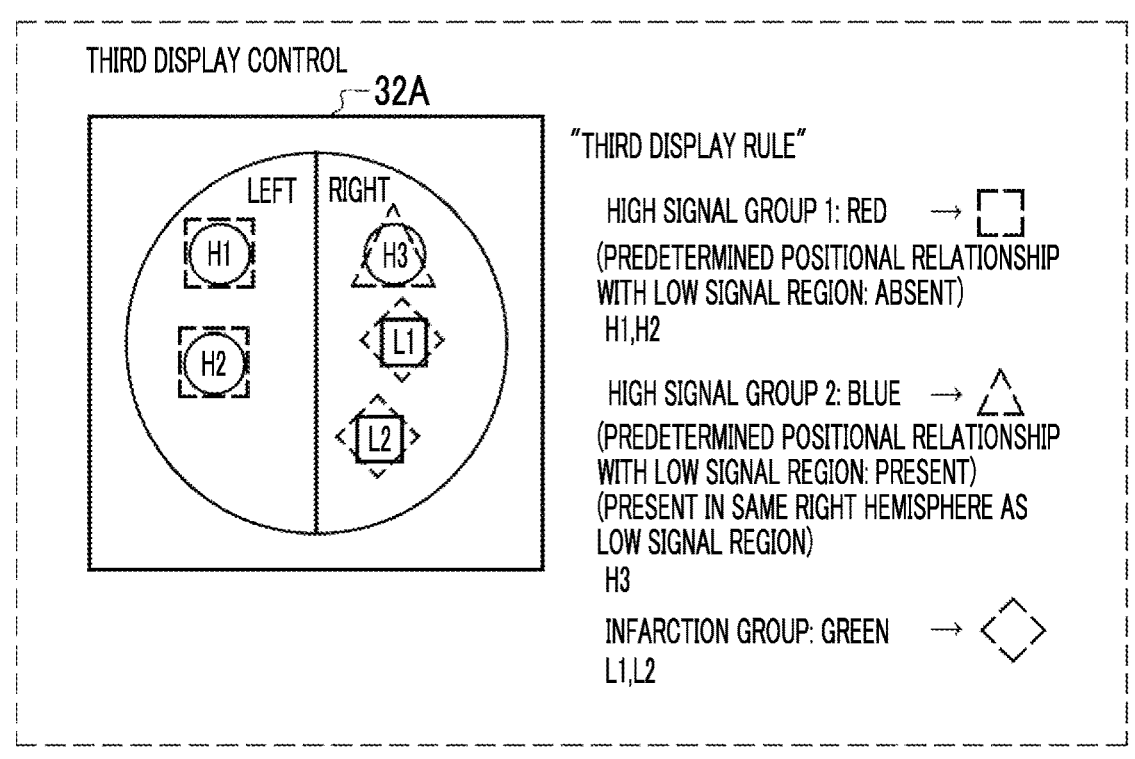

THIRD DISPLAY CONTROL

"THIRD DISPLAY RULE"

HIGH SIGNAL GROUP 1: RED          →  ☐
(PREDETERMINED POSITIONAL RELATIONSHIP
WITH LOW SIGNAL REGION: ABSENT)
H1,H2

HIGH SIGNAL GROUP 2: BLUE          →  △
(PREDETERMINED POSITIONAL RELATIONSHIP
WITH LOW SIGNAL REGION: PRESENT)
(PRESENT IN SAME RIGHT HEMISPHERE AS
LOW SIGNAL REGION)
H3

INFARCTION GROUP: GREEN          →  ◇
L1,L2

MEDICAL SUPPORT DEVICE, AND OPERATION METHOD AND OPERATION PROGRAM OF MEDICAL SUPPORT DEVICE

CROSS-REFERENCE TO RELATED APPLICATIONS

The present application claims priority under 35 U.S.C. § 119 to Japanese Patent Application No. 2022-060859 filed on Mar. 31, 2022. The above application is hereby expressly incorporated by reference, in its entirety, into the present application.

BACKGROUND

1. Technical Field

A technique of the present disclosure relates to a medical support device, and an operation method and an operation program of a medical support device.

2. Description of the Related Art

JP2019-213785A discloses a technique that determines a bleeding region based on a signal value of a brain image as an example of a medical image.

SUMMARY

The technique of the present disclosure relates to display of an abnormal signal region of a medical image, and provides a medical support device, and an operation method and an operation program of a medical support device with improved convenience for a user.

A medical support device according to the technique of the present disclosure is a medical support device comprising a processor, in which the processor is configured to execute first display control for displaying abnormal signal regions detected by performing image analysis on a medical image, in an identifiable manner and second display control for changing a display aspect for each group classified by an operation instruction, on the abnormal signal regions.

An operation method of a medical support device according to the technique of the present disclosure is an operation method of a medical support device including a processor, the operation method comprising executing, by the processor, first display control for displaying abnormal signal regions detected by performing image analysis on a medical image, in an identifiable manner and second display control for changing a display aspect for each group classified by an operation instruction, on the abnormal signal regions.

An operation program of a medical support device according to the technique of the present disclosure is an operation program that causes a computer to function as a medical support device, the operation program causing the computer to execute first display control for displaying abnormal signal regions detected by performing image analysis on a medical image, in an identifiable manner and second display control for changing a display aspect for each group classified by an operation instruction, on the abnormal signal regions.

BRIEF DESCRIPTION OF THE DRAWINGS

Exemplary embodiments according to the technique of the present disclosure will be described in detail based on the following figures, wherein:

FIG. 12 is a diagram showing an example of second list setting information, FIG. 13 is a diagram schematically showing first display control and second display control, FIG. 15 is a diagram schematically showing third display control, FIG. 17 is a diagram showing a combination example of second display control and third display control.

DETAILED DESCRIPTION

First Embodiment

Figure 1:
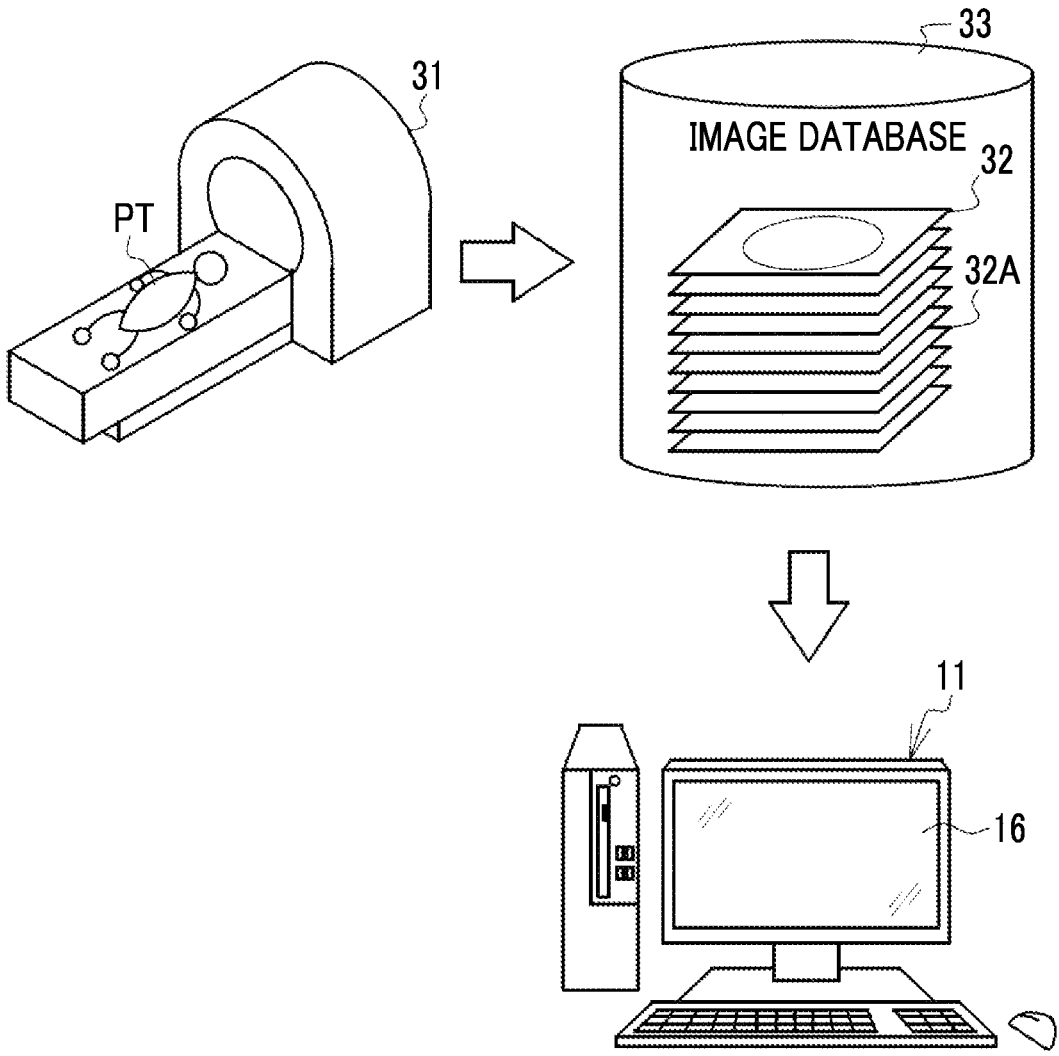
FIG. 1 is a diagram showing a medical support device.

A medical support device 11 shown in FIG. 1 comprises a display 16, and outputs a tomographic image 32A of a subject PT to the display 16. The tomographic image 32A is an example of a "medical image". The medical support device 11 acquires a tomographic image group 32 from an image database 33 connected to be communicable thereto, for example. The image database 33 is, for example, a picture archiving and communication system (PACS) server, and stores the tomographic image group 32. A tomography apparatus 31 captures the tomographic image group 32. In the present example, the tomography apparatus 31 is a computed tomography (CT) apparatus. As well known in the art, the CT apparatus acquires a CT value while rotating a radiation source and a radiation detector around a body axis of the subject PT. The acquisition of the CT value is performed at each position in a body axis direction by scanning the radiation source and the radiation detector in the body axis direction of the subject PT. The CT value is a radiation absorption value in the body of the subject PT. The CT apparatus generates the tomographic image 32A by executing image reconstruction processing based on the CT value acquired in each direction around the body axis. Each tomographic image 32A is a two-dimensional image generated depending on a slice thickness in the body axis direction, and the tomographic image group 32 is a set of a plurality of tomographic images 32A corresponding to respective positions in the body axis direction. The tomographic image group 32 is output from the tomography apparatus 31 to the image database 33.

Figure 2:
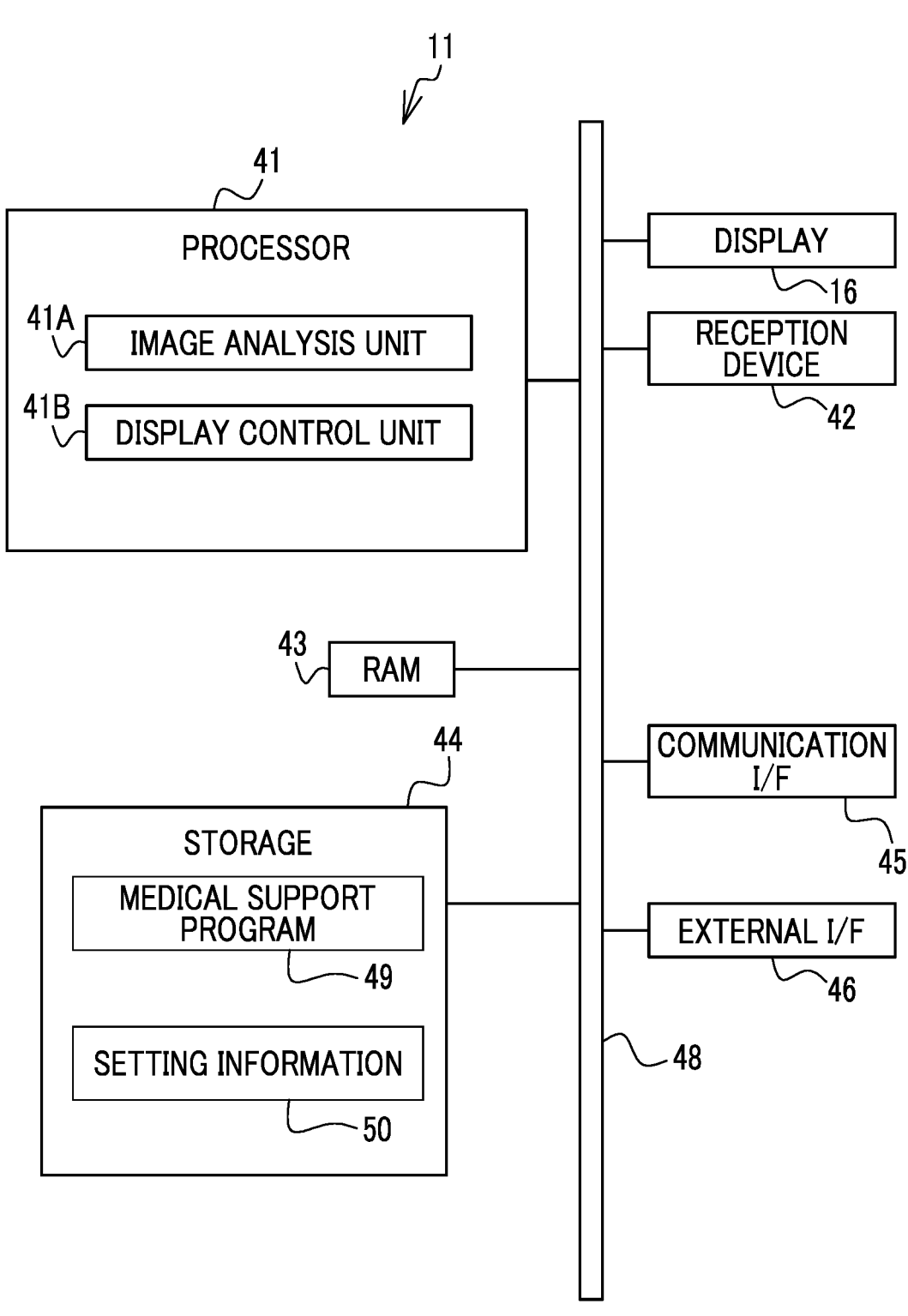
FIG. 2 is a diagram showing the hardware configuration of the medical support device.

In FIG. 2, an example of the hardware configuration of the medical support device 11 is shown. The medical support device 11 is an example of a "medical support device" and a "computer" according to the technique of the present disclosure, and comprises a processor 41, a reception device 42, a display 16, a random access memory (RAM) 43, a storage 44, a communication I/F 45, and an external I/F 46. The units are connected to a bus 48 and can communicate with each other.

The medical support device 11 is operated by a user, such as a physician, through the reception device 42. The reception device 42 has a keyboard, a mouse, and the like (not shown), and receives an instruction from an operator. The reception device 42 may be a device that receives a touch input, such as a touch panel, a device that receives a voice input, such as a microphone, a device that receives a gesture input, such as a camera, or the like.

Examples of the display 16 include an electro-luminescence (EL) display and a liquid crystal display. In addition to a medical image, such as the tomographic image 32A, various kinds of information are displayed on the display 16.

The processor 41 is, for example, a central processing unit (CPU), and integrally controls each unit of the medical support device 11 following a control program and executes various kinds of processing following various kinds of application programs.

The storage 44 is a non-volatile storage device that stores various kinds of programs, various kinds of setting information 50, and the like. Examples of the storage 44 include a hard disk drive (HDD) and a solid state drive (SSD). In the storage 44, a medical support program 49 that causes a computer to function as the medical support device 11 is stored. The setting information 50 includes setting information regarding the display of the tomographic image 32A, and the like as described below.

The RAM 43 is a memory where information is temporarily stored, and is used as a work memory by the processor 41. An example of the RAM 43 is a dynamic random access memory (DRAM) or a static random access memory (SRAM).

The communication I/F 45 is connected to a network (not shown), such as a local area network (LAN) and/or a wide area network (WAN), and performs transmission control following a communication protocol defined in various kinds of wired or wireless communication standards. The processor 41 acquires the tomographic image 32A from the image database 33 through the communication I/F 45.

The external I/F 46 is, for example, a universal serial bus (USB) interface, and is used for connection to peripheral equipment, such as a printer and a memory card.

The processor 41 executes medical support processing by reading out the medical support program 49 from the storage 44 and executing the medical support program 49 on the RAM 43. The medical support processing is realized by the processor 41 operating as an image analysis unit 41A and a display control unit 41B. The medical support program 49 is an example of an "operation program of a medical support device" according to the technique of the present disclosure.

The processor 41 performs image analysis on the tomographic image 32A by functioning as the image analysis unit 41A. The processor 41 controls the display of the tomographic image 32A and an analysis result of the tomographic image 32A on the display 16 by functioning as the display control unit 41B.

The medical support device 11 provides information useful for diagnosis by displaying an abnormal signal region where a signal value is abnormal, in the tomographic image 32A as an analysis result. The abnormal signal region refers to a region where the signal value shows an abnormal value compared to a normal case, in a region of a medical image where an organ is rendered. Specifically, the abnormal signal region is a region where a difference in signal value from a signal value (including a peripheral representative value (average value or median value) of a peripheral region is large, a region where a deviation from a normal signal value of a certain region is large (for example, a region where a difference from a threshold value is outside an allowable range), or the like, and includes a region detected by a machine learning model.

The CT value is an example of a "signal value" according to the technique of the present disclosure. The CT value is a radiation (for example, X-rays) absorption value, and more specifically, is obtained by converting a radiation absorption value of each part in the body into a numerical value in a case where water is "0" and air is "−1000". The unit of the CT value is "HU: Hounsfield Unit" (see FIG. 5 and the like). The CT value is expressed as a brightness value in the tomographic image 32A. As a larger amount of X-rays is absorbed, the CT value that is the signal value is higher, and the display is performed with lower density in the tomographic image 32A (approaches white). On the contrary, as a smaller amount of X-rays is absorbed, the CT value that is the signal value is lower, and the display is performed with a higher density in the tomographic image 32A (approaches black). For example, in comparison of a bone and a soft tissue, since the bone absorbs a large amount of X-rays, the bone has a high CT value, and is low in density in the tomographic image 32A (near white). On the contrary, the soft tissue has a low CT value, and is high in density in the tomographic image 32A (near black).

In the abnormal signal region, as an example, there are a high signal region where the signal value is relatively high and a low signal region where the signal value is relatively low. A normal range of the signal value is determined, for example, for each part of the organ, the high signal region has the signal value higher than the normal range, and the low signal region has the signal value lower than the normal range. The high signal region is an example of a "first abnormal signal region" according to the technique of the present disclosure, and the low signal region is an example of a "second abnormal signal region" according to the technique of the present disclosure.

Figure 3:
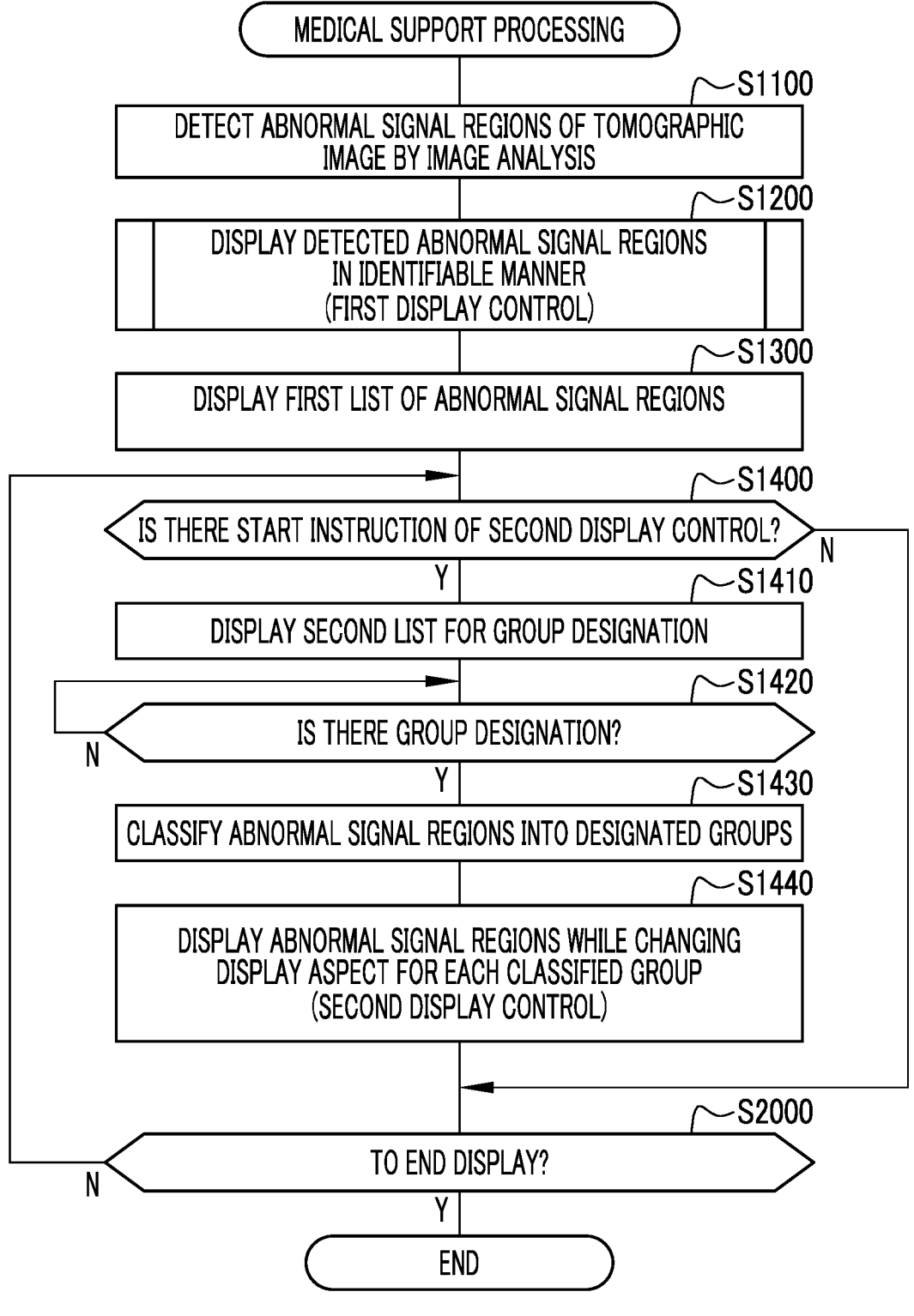
FIG. 3 is a flowchart illustrating a processing procedure of entire medical support processing.
Figure 4:
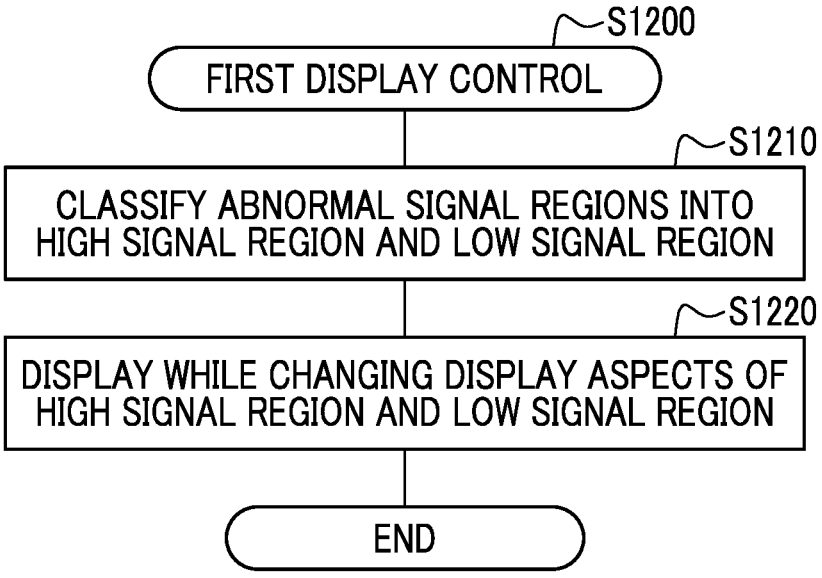
FIG. 4 is a flowchart illustrating a processing procedure of first display control.

FIG. 3 is an example of a flowchart illustrating the entire procedure of the medical support processing that is executed by the processor 41, and FIG. 4 is an example of a flowchart illustrating a procedure of a part of the processing shown in FIG. 3. Hereinafter, the medical support processing that is executed by the processor 41 will be described referring to image display screen examples of FIGS. 5 to 12 and the like as appropriate, in addition to the flowcharts of FIGS. 3 and 4.

As shown in FIG. 3, in Step S1100, the processor 41 detects abnormal signal regions of the tomographic image 32A by image analysis. Next, in Step S1200, the detected abnormal signal regions are displayed in an identifiable manner. The processing of Step S1200 is referred to as first display control.

More specifically, the first display control of Step S1200 is performed in a procedure shown in FIG. 4. First, in Step S1210, the processor 41 classifies the detected abnormal signal regions into a high signal region and a low signal region in the present example. Then, in Step S1220, the processor 41 displays the high signal region and the low signal region in the tomographic image 32A while changing display aspects.

In Step S1300 shown in FIG. 3, the processor 41 displays a list of the detected abnormal signal regions as a first list 51 (see FIG. 5 and the like) separately from the display of the abnormal signal regions in the tomographic image 32A.

Figure 5:
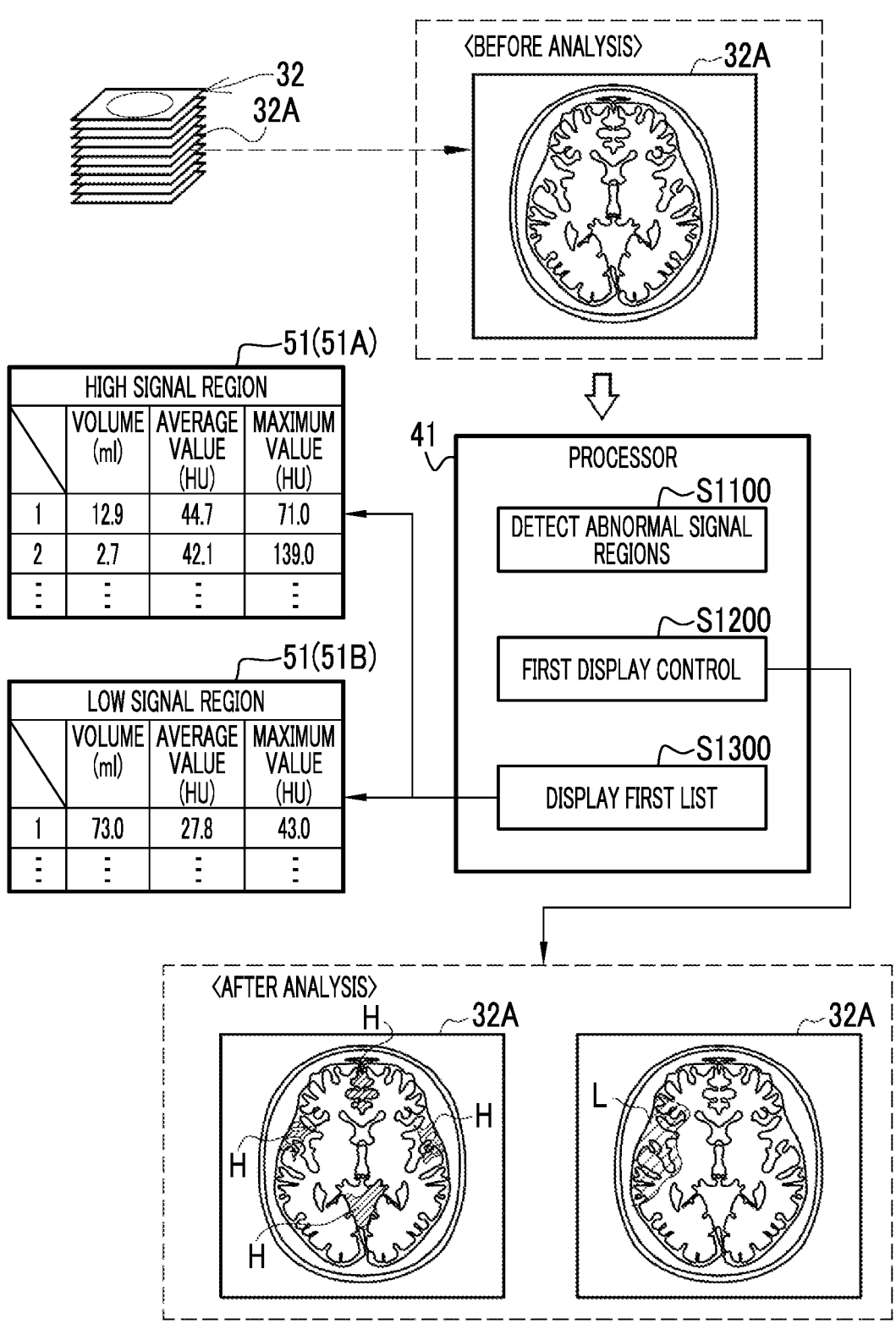
FIG. 5 is a diagram schematically showing processing of abnormal signal detection, first display control, and first list display.

The processing of Steps S1100 to S1300 will be schematically described referring to FIG. 5. The tomographic image 32A is a brain image where an axial cross section of a brain is rendered, as an example. In Step S1100, the processor 41 detects the abnormal signal regions in the tomographic image 32A by performing, for example, semantic segmentation using a machine learning model as image analysis on the tomographic image 32A.

The machine learning model is, for example, UNET that is an example of a convolutional neural network (CNN). UNET is a representative machine learning model that is used for image recognition for identifying an object, a region, or the like in an image. UNET extracts a feature quantity of an image by executing a plurality of kinds of filtering processing for each hierarchy having a different image size while hierarchically reducing an image size of an input image. The feature quantity is extracted for each hierarchy having a different image size, whereby a global feature quantity and a local feature quantity of the image can be extracted. UNET identifies abnormal signal regions in the image based on such feature quantities and outputs an image in which the identified abnormal signal regions are segmented.

The machine learning model performs learning, for example, with a past case image and correct answer data in which an abnormal signal region in the case image is labeled, as learning data. Here, labeling an abnormal signal region indicates, for example, attaching a label that is different from a label attached to a pixel included in a normal signal region and indicates the abnormal signal region, to a pixel included in the abnormal signal region. In a case where the machine learning model is required to identify the abnormal signal regions while further distinguishing between the high signal region and the low signal region, the machine learning model is trained using correct answer data in which different labels are attached to the high signal region and the low signal region. An image analysis method for detecting an abnormal signal region is not limited to the image analysis method using the machine learning model, and a rule-based image analysis method, such as pattern matching, may be used.

Then, in Step S1200, the processor 41 performs first display control on the detected abnormal signal regions. In FIG. 5, out of two tomographic images 32A after analysis subjected to image analysis by the processor 41, a left tomographic image 32A is an image including a high signal region H as an abnormal signal region, and a right tomographic image 32A is an image including a low signal region L as an abnormal signal region. Each of the high signal region H and the low signal region L is displayed in a display aspect identifiable from the other region.

Here, the display aspect is a concept including any of color, brightness, pattern, and the like. The color is a concept including, for example, any of hue, chroma saturation, and lightness, and the pattern is a concept including, for example, hatching. A form of a bounding box that surrounds an abnormal signal region by a polygon including a rectangle, a circle, or the like is also included in the display aspect. In summary, the display aspect is a concept including all aspects identifiable from the other region. In the present example, in the monochromatic tomographic images 32A, the high signal region H is red-hatched, and the low signal region L is blue-hatched. In this way, two kinds of abnormal signal regions of the high signal region H and the low signal region L are color-hatched, and accordingly, are displayed to be identifiable from a normal signal region. The high signal region H and the low signal region L are allocated with different colors of red and blue, so that both the high signal region H and the low signal region L can be identified. In FIG. 5, the tomographic image 32A in which the high signal region H is included and the tomographic image 32A in which the low signal region L is included are shown as separate images of different tomographic positions. There is of course also a case where the high signal region H and the low signal region L are mixed in one tomographic image 32A.

The processor 41 displays the first list 51 in Step S1300. As shown in FIG. 5, in the present example, the processor 41 classifies abnormal signal regions into two regions of a high signal region H and a low signal region L, and displays the first list 51 while dividing the first list into two lists of high signal regions H and low signal regions L. A first list 51A is a list of high signal regions H detected by image analysis, and a first list 51B is a list of low signal regions L detected by image analysis. Hereinafter, the first lists 51A and 51B are simply referred to as the first list 51 in a case where there is no need for distinction therebetween. The first list 51 is an example of a "first list" according to the technique of the present disclosure. In the first lists 51A and 51B, volume and an average value and a maximum value of the CT value are displayed for each region of the detected high signal regions H and low signal regions L. The reason that the volume is shown instead of an area is because the tomographic image group 32 is a set of a plurality of tomographic images 32A stacked in a thickness direction. That is, one abnormal signal region is present three-dimensionally over a plurality of tomographic images 32A.

Figure 6:
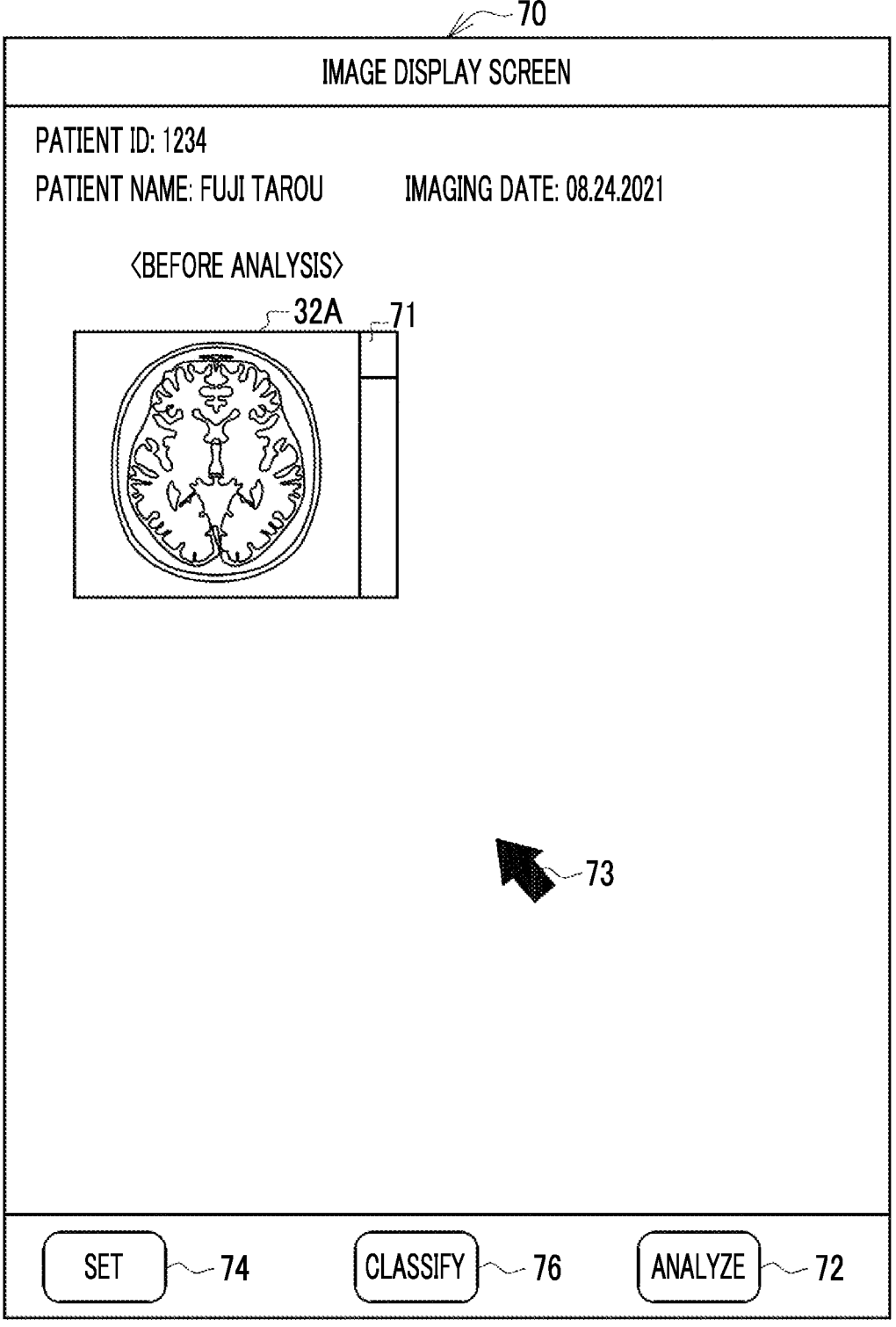
FIG. 6 is a diagram showing an example of an image display screen.

An image display screen 70 shown in FIG. 6 is an example of a screen on which the tomographic image 32A is displayed in the medical support device 11. In the image display screen 70, bibliographic items, such as a patient identification (ID), a patient name, and an imaging date of the subject PT, are displayed in an upper portion, and a region where an image is displayed is provided below the bibliographic items. On the image display screen 70 shown in FIG. 6, only the tomographic image 32A before analysis is displayed. Reference numeral 71 denotes a scroll bar for switching between a plurality of tomographic images 32A at different tomographic positions.

At a lower end of the image display screen 70, an ANALYZE button 72, a SET button 74, and a CLASSIFY button 76 are provided. The ANALYZE button 72 is an operation button for inputting an operation instruction to cause the processor 41 to execute image analysis. The SET button 74 is an operation button for performing a switching operation of display contents and various kinds of setting operations regarding display. The CLASSIFY button 76 is an operation button that is used for classification of abnormal signal regions as described below. In this way, the image display screen 70 is an operation screen that is used for an operation. The image display screen 70 is an example of an "operation screen" according to the technique of the present disclosure. Reference numeral 73 denotes a pointer, and is operated by a mouse or the like and used to operate the ANALYZE button 72, the SET button 74, and the like.

Figure 7:
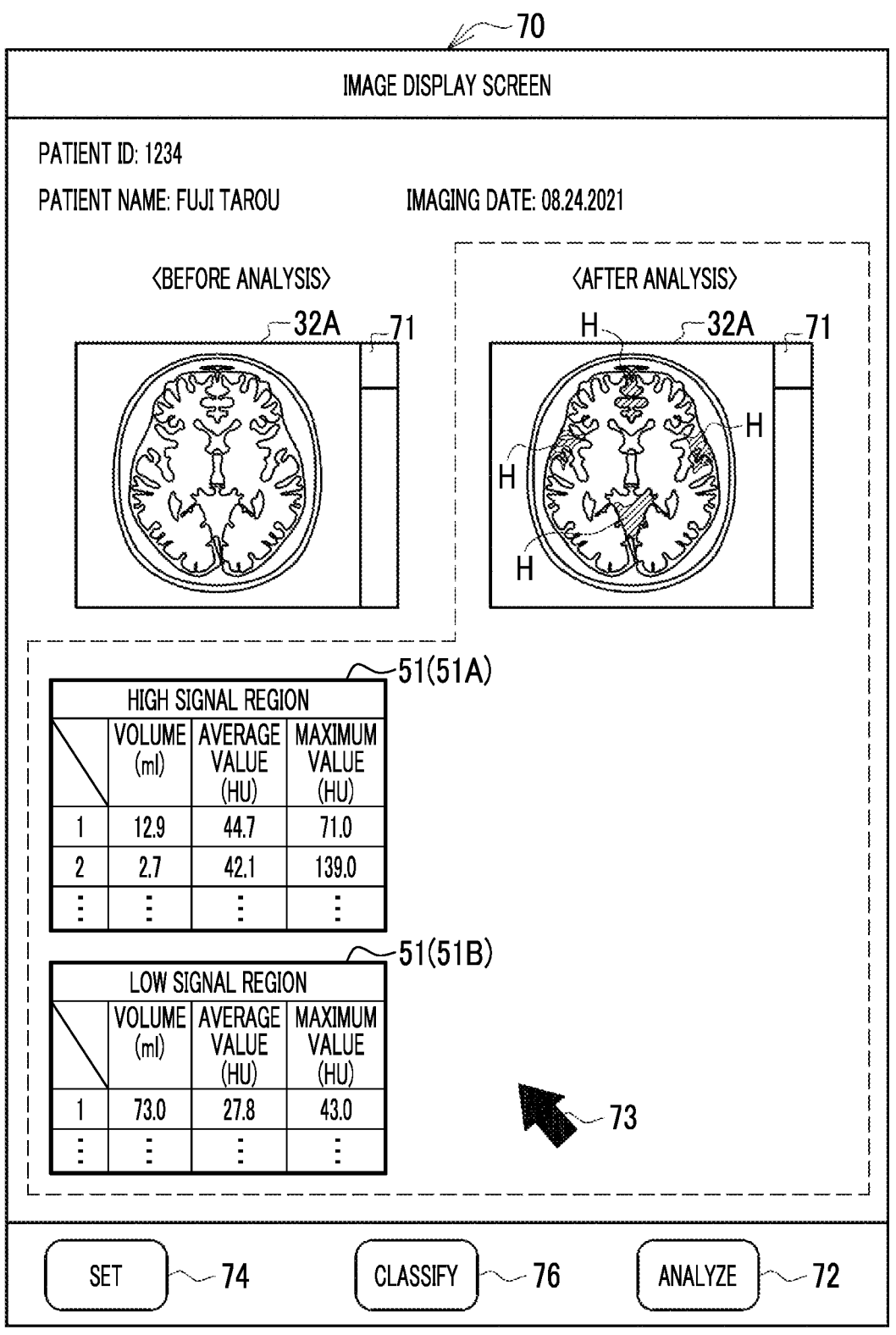
FIG. 7 is an example of an image display screen on which an analysis result of a high signal region is displayed.
Figure 8:
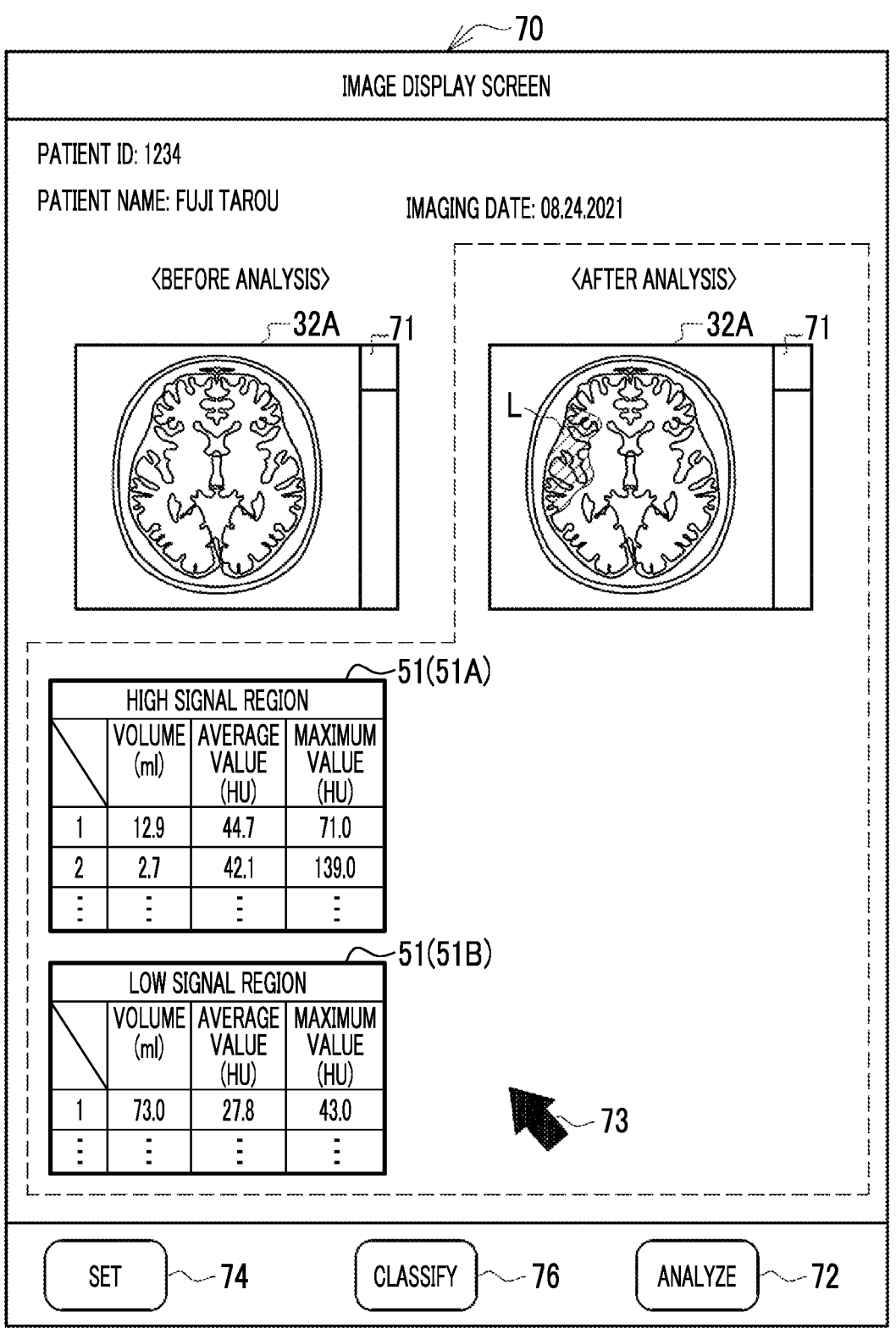
FIG. 8 is an example of an image display screen on which an analysis result of a low signal region is displayed.

In a case where image analysis is executed on the tomographic image 32A, as shown in FIGS. 7 and 8, an analysis result is displayed on the image display screen 70. As an example, the analysis result is display of high signal regions H and low signal regions L in the tomographic images 32A, and the first list 51A as a list of the high signal regions H and the first list 51B as a list of the low signal regions L. FIG. 7 is a display example of the analysis result of the tomographic image 32A in which the high signal region H is detected, and FIG. 8 is a display example of the analysis result of the tomographic image 32A in which the low signal region L is detected. In the present example, although an example where the tomographic image 32A after analysis is displayed one by one in the image display screen 70 has been shown, a plurality of tomographic images 32A shown in FIGS. 7 and 8 may be displayed in parallel in the image display screen 70.

Figure 9:
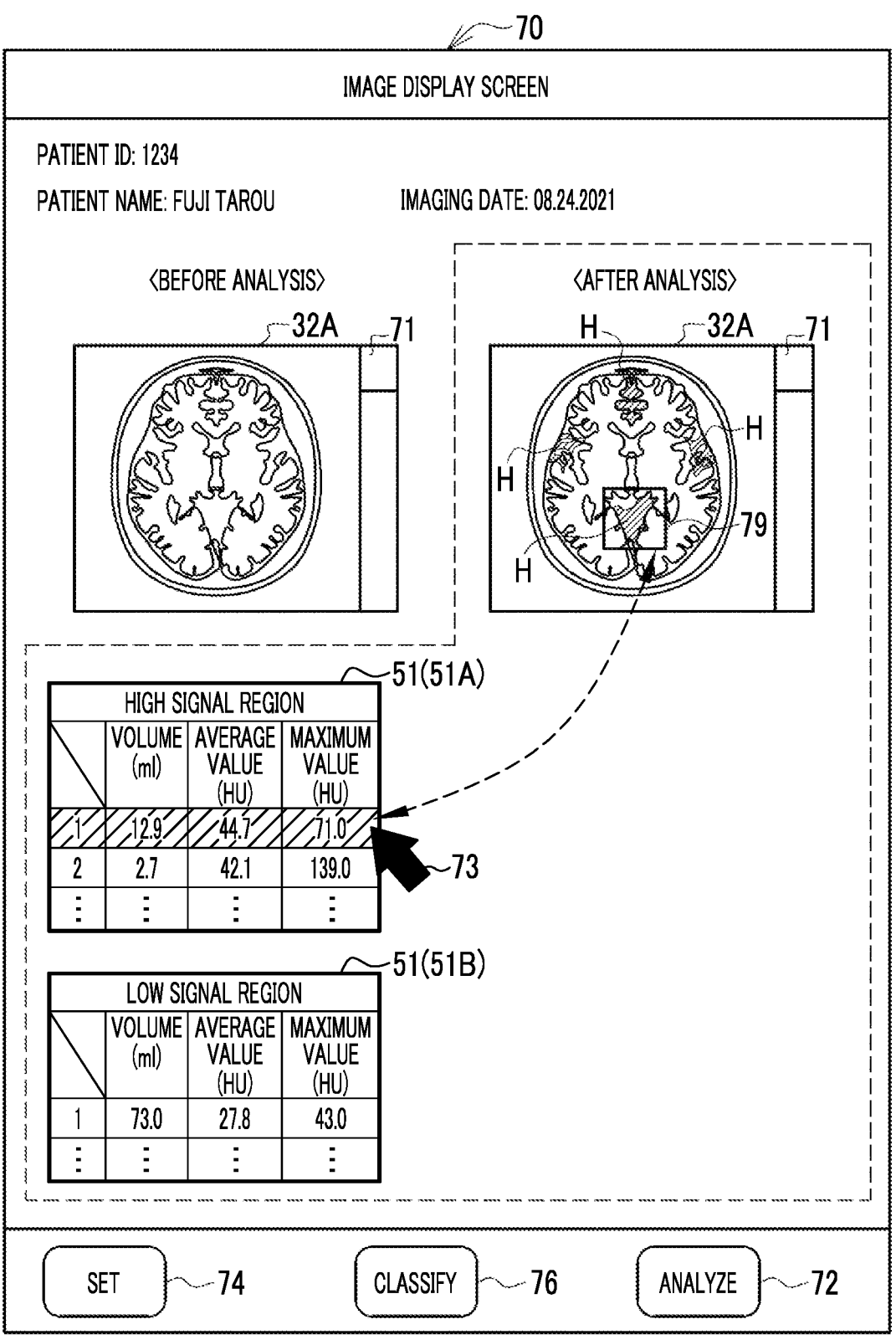
FIG. 9 is a diagram showing an example of a method of showing a correspondence relationship between abnormal signal regions of a first list and a tomographic image.

The user can ascertain a correspondence relationship between the abnormal signal regions in the first list 51 and the abnormal signal regions on the tomographic image 32A, for example, by a method illustrated in FIG. 9. The method shown in FIG. 9 is a method in which, in a case where one abnormal signal region in one of the first list 51 or the tomographic image 32A is selected by the pointer 73, the corresponding abnormal signal region in the other one is highlighted with respect to other abnormal signal regions.

More specifically, FIG. 9 shows a state in which one of a plurality of high signal regions H included in the first list 51 is selected by the pointer 73. In this state, meshing or the like is applied to a row where the selected high signal region H is displayed, in the first list 51. With this, the row of the selected high signal region H in the first list 51 is highlighted with respect to the rows of other high signal regions H. In a case where one high signal region H in the first list 51 is selected by the pointer 73, the processor 41 extracts the tomographic image 32A including the corresponding high signal region H from the tomographic image group 32. Then, the processor 41 displays a rectangular bounding box 79 or the like for the corresponding high signal region H on the extracted tomographic image 32A. With this, the corresponding high signal region H in the tomographic image 32A is highlighted with respect to other high signal regions H. In FIG. 9, an arc-shaped two-way arrow shown by a dotted line shows that one high signal region H in the first list 51 selected by the pointer 73 corresponds to one high signal region H on the tomographic image 32A highlighted by the bounding box 79.

In the example shown in FIG. 9, although an example where one high signal region H in the first list 51 is selected by the pointer 73 has been shown, on the contrary, in a case where one high signal region H in the tomographic image 32A is selected by the pointer 73, the row where the corresponding high signal region H is displayed, in the first list 51 is highlighted with respect to the rows where other high signal regions H are displayed.

Here, highlighting may be display in which an abnormal signal region to be highlighted has improved visibility than the abnormal signal regions other than the abnormal signal region to be highlighted. A method of highlighting may be highlighting for improving brightness of the abnormal signal region to be highlighted, instead of meshing the abnormal signal region to be highlighted or surrounding the abnormal signal region to be highlighted by the bounding box 79 as shown in the present example.

In the example shown in FIG. 9, although an example where the corresponding high signal regions H in both the first list 51 and the tomographic image 32A are highlighted has been shown, the high signal region H in only one of the first list 51 and the tomographic image 32A may be highlighted. For example, in a case where one high signal region H in the first list 51 is selected by the pointer 73, the high signal region H in the first list 51 may not be highlighted, and only the corresponding high signal region H in the tomographic image 32A may be highlighted. This is because, even though the high signal region H selected by the pointer 73 is not particularly highlighted, the user can ascertain the selected high signal region H from the presence of the pointer 73. In the example of FIG. 9, although the high signal region H has been described as the abnormal signal region as an example, the same also applies to the low signal region L.

The user can ascertain the correspondence relationship between the abnormal signal region in the first list 51 and the abnormal signal region on the tomographic image 32A by the above-described method illustrated in FIG. 9.

Returning to FIG. 3, after Step S1300, the processor 41 proceeds to Step S1400. Steps S1400 to S1440 are processing steps regarding second display control. The second display control is display control for changing a display aspect for each group classified by an operation instruction, on the detected abnormal signal regions. Designation on a group into which an abnormal signal region is classified is performed by the user. First, in Step S1400, the processor 41 waits for an input of a start instruction of the second display control from the user. The start instruction of the second display control is input by an operation of the CLASSIFY button 76 on the image display screen 70.

In a case where the start instruction of the second display control is input by the operation of the CLASSIFY button 76 (in Step S1400, Y), the processor 41 displays a second list 85 (see FIG. 10) for group designation on the image display screen 70 (Step S1410). The second list 85 is a list that is generated for each group into which the abnormal signal regions are classified, and is able to display the abnormal signal regions classified into the group. The second list 85 is an example of a "second list" according to the technique of the present disclosure.

Then, in Step S1420, the processor 41 receives the group designation as the operation instruction for classifying the abnormal signal region into the group. In a case where the group designation is input (in Step S1420, Y), in Step S1430, the processor 41 classifies the abnormal signal region into the designated group. The group designation is performed for each abnormal signal region. In Step S1430, the processor 41 displays the abnormal signal regions classified into the group in the second list 85.

In Step S1440, the processor 41 executes the second display control for displaying the abnormal signal regions while changing the display aspect for each classified group, in the tomographic image 32A. The processor 41 repeats the processing of Steps S1400 to S1440 until the display of the tomographic image 32A ends (Step S2000).

Figure 10:
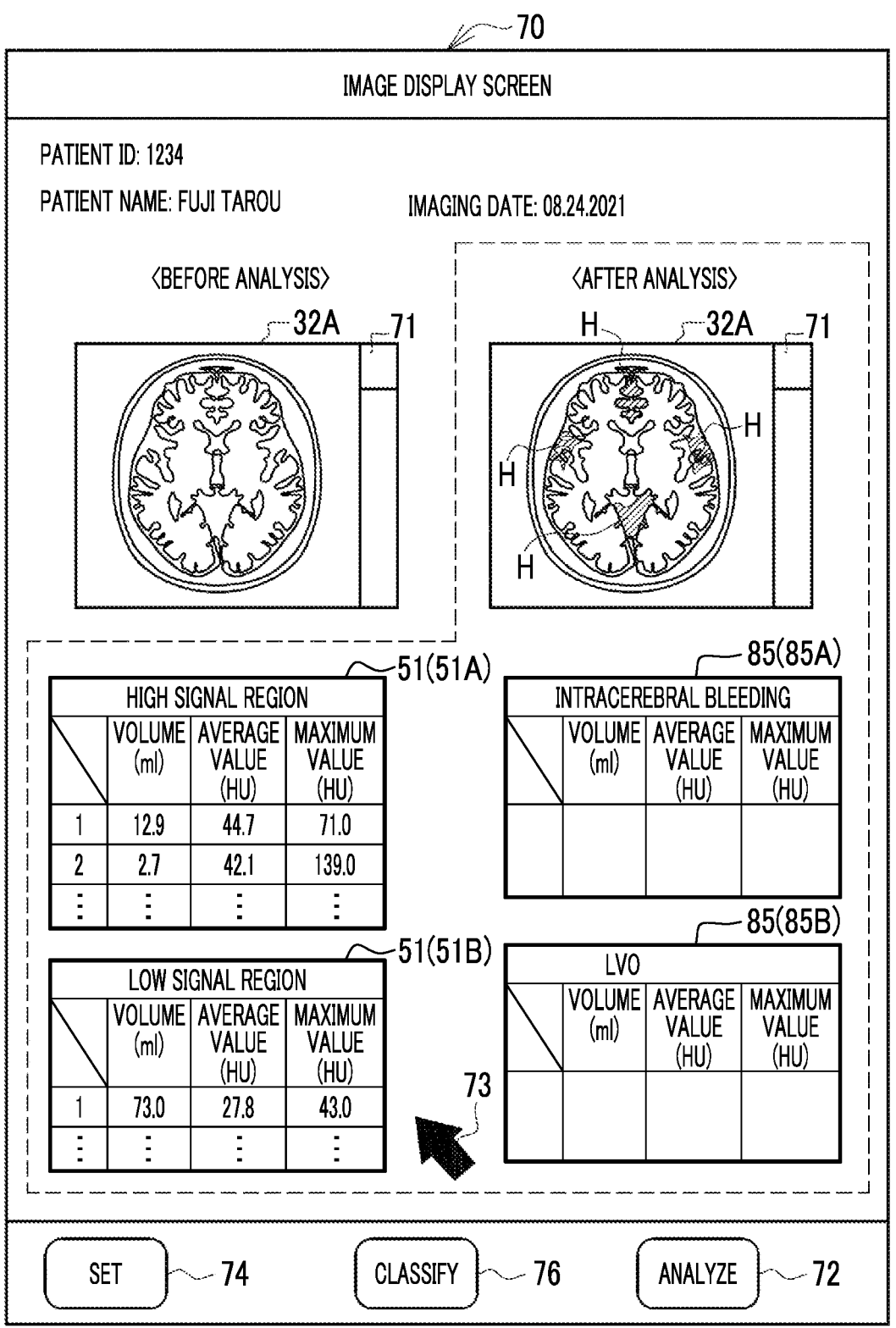
FIG. 10 is an example of an image display screen on which a second list before classification of abnormal signal regions is displayed.
Figure 11:
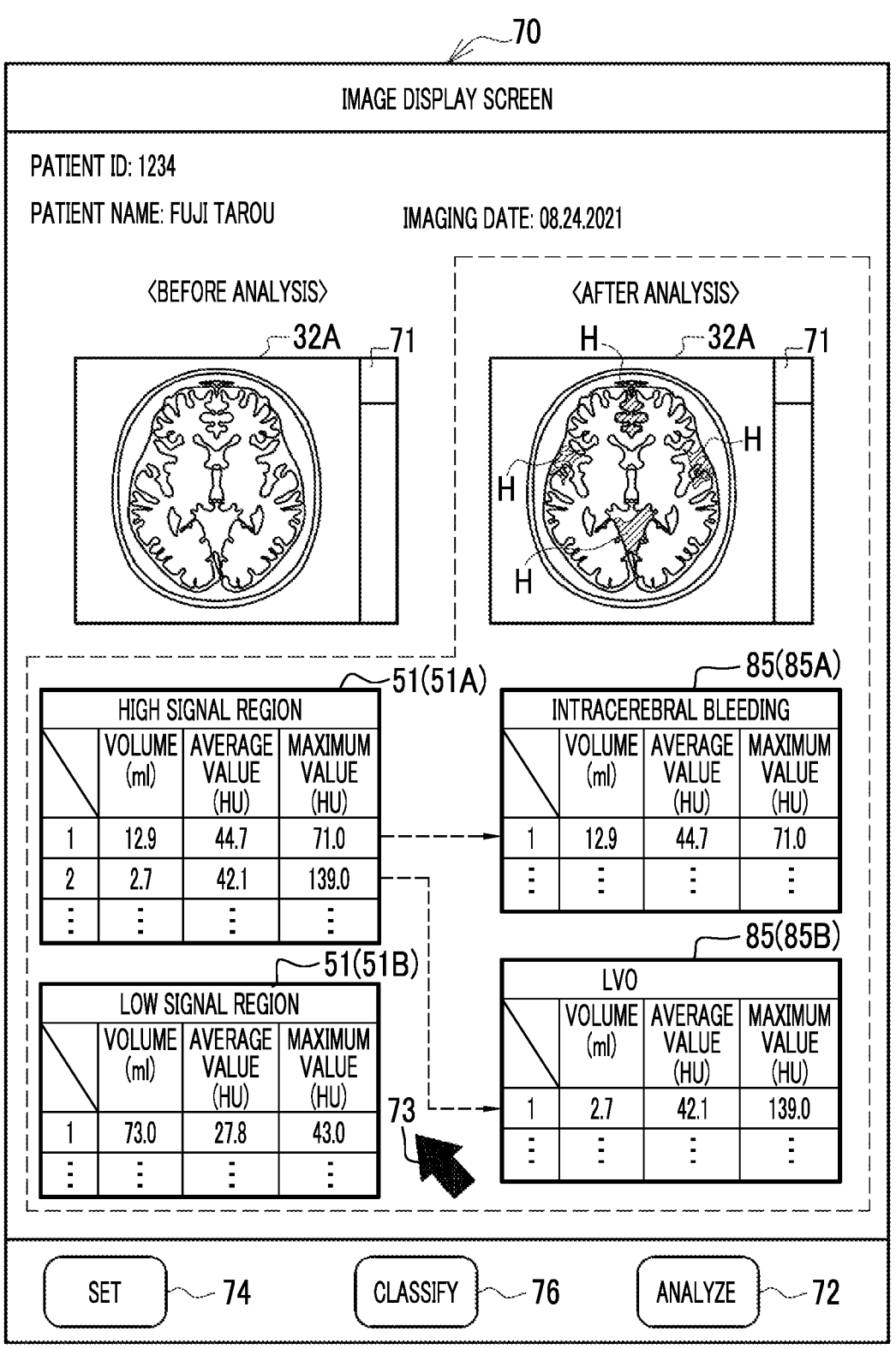
FIG. 11 is an example of an image display screen on which a second list after classification of abnormal signal regions is displayed.

The processing regarding the second display control until Steps S1400 to S1440 of FIG. 3 will be specifically described referring to FIGS. 10 and 11. The first lists 51A and 51B are lists that display all the abnormal signal regions detected by the image analysis. In contrast, the second list 85 is a list for group designation for classifying the abnormal signal regions into the groups. In FIGS. 10 and 11, two lists of second lists 85A and 85B are illustrated as the second list 85. Hereinafter, the second lists 85A and 85B are simply referred to as the second list 85 in a case where there is no need for distinction therebetween. The user can designate a group into which the abnormal signal region is classified, in the second list 85.

The user can optionally set the group of the second list 85, and the processor 41 displays the second list 85 for each group. Each group of the second list 85 can be set for each finding of the abnormal signal region, and in this case, the processor 41 displays a name of the finding as a group name of the second list 85. Such a second list 85 is used to classify each abnormal signal region into a group of each finding that is an evaluation for each abnormal signal region by the user. In FIG. 10, the second list 85 is in an empty state in which the abnormal signal region is unclassified.

In the present example, as shown in FIG. 10, a finding "intracerebral bleeding" is set for the second list 85A, and a finding "LVO: Large vessel occlusion" is set for the second list 85B. A physician as a user observes the high signal region H, the low signal region L, and the like of the tomographic image 32A, and gives a finding for each abnormal signal region. For example, in a case where the user gives the finding "intracerebral bleeding" on one high signal region H in the tomographic image 32A, the high signal region H is selected from the first list 51A, and is classified into a group "intracerebral bleeding" of the second list 85A. Similarly, in a case where the user gives the finding "LVO" on one high signal region H in the tomographic image 32A, the high signal region H is selected from the first list 51A, and is classified into a group "LVO" of the second list 85B. The abnormal signal regions of both "intracerebral bleeding" and "LVO" are the high signal regions H where the signal value is relatively high, in the tomographic image 32A.

As described referring to FIG. 9, in a case where the abnormal signal region in the tomographic image 32A is selected by the pointer 73, the row of the selected abnormal signal region in the first list 51 is highlighted. In addition, the corresponding abnormal signal region on the tomographic image 32A is highlighted. With this, the user can ascertain the correspondence relationship between the abnormal signal region on the tomographic image 32A and the abnormal signal region in the first list 51. Even in a case where the abnormal signal region in the second list 85 is selected, highlighting is performed by the method shown in FIG. 9 as in the case of the first list 51. With this, the user can also ascertain a correspondence relationship between the abnormal signal region after classification in the second list 85 and the abnormal signal region on the tomographic image 32A.

The group designation of the abnormal signal region is performed by an operation to select the abnormal signal region included in the first lists 51A and 51B by the pointer 73 and to drag the abnormal signal region to any of the second lists 85A and 85B, for example, as indicated by an arrow of a dotted line in FIG. 11.

FIG. 12 is an example of second list setting information 50A. The second list setting information 50A is information indicating a relationship between the groups of the second list 85 and the display aspects of the respective groups. In the present example, in regard to a finding that is set as a group of the second list 85, a finding specialized for diagnosis regarding an injury and a disease of a brain, such as a stroke, is set. In the second list setting information 50A, in regard to the high signal region H, findings, such as "subarachnoidal bleeding", "intracerebral bleeding", "LVO", "Hyperdense Sign", and "calcification", are set. In regard to the low signal region L, "infarction" and the like are set. The user can optionally set the group into which the abnormal signal region is classified or the display aspect corresponding to the group by editing the second list setting information 50A. The number of groups can also be increased or decreased. The name of the finding can be set as the group name by editing the second list setting information 50A.

Similarly to the second list setting information 50A, first list setting information may be provided. The first list setting information is information regarding a relationship between the groups of the first list 51 and the display aspects of the respective groups. Examples of the groups of the first list 51 include groups of an abnormal signal region and a normal signal region or groups of a high signal region and a low signal region. The user may optionally set the display aspect corresponding to each group by editing the first list setting information.

In the second list setting information 50A, the display aspect is set for each group in such a manner that "P1" is set for "subarachnoidal bleeding", and "P2" is set for "intracerebral bleeding". The processor 41 displays the abnormal signal region classified into the second list 85 in the tomographic image 32A following the display aspect defined in the second list setting information 50A.

FIG. 13 is a diagram schematically showing the first display control of Step S1200 and the second display control of Step S1440. The first display control is control for displaying abnormal signal regions detected by performing image analysis on a tomographic image 32A in an identifiable manner as described above. In the present example, the abnormal signal regions are classified into the high signal region H and the low signal region L depending on the signal value, and the display aspect of each of the high signal region H and the low signal region L is changed. The first display control is executed following a first display rule. In the first display rule of the present example, the display aspect of the high signal region H is set as red-hatching. In FIG. 13, red-hatching is shown by a dotted line quadrangle. The display aspect of the low signal region L is set as blue-hatching. In FIG. 13, blue hatching is shown by a triangle of a dotted line.

A right and a left in the tomographic image 32A that schematically shows a brain image means a right hemisphere and a left hemisphere of a brain, respectively. In the tomographic image 32A shown in FIG. 13, while the number of high signal regions H is two ("H1" and "H2") in the left hemisphere and is one ("H3") in the right hemisphere, in the first display control, all the three high signal regions H of "H1" to "H3" are red-hatched following the first display rule. On the other hand, in the tomographic image 32A shown in FIG. 13, the number of low signal regions L is two ("L1" and "L2") in the right hemisphere. Both the two low signal regions L of "L1" and "L2" are blue-hatched following the first display rule. In this way, in the first display control, each of the abnormal signal regions of the high signal region H and the low signal region L in the tomographic image 32A is displayed to be identifiable from other regions. In the present example, the display aspect is changed between the high signal region H and the low signal region L in such a manner that the high signal region H is red-hatched and the low signal region L is blue-hatched.

On the other hand, in the second display control, the processor 41 changes the display aspect for each group classified by the operation instruction, on the abnormal signal regions. In the second display control, the display aspect of the abnormal signal region is changed following a second display rule. The second display rule of FIG. 13 is an example of contents defined in the second list setting information 50A shown in FIG. 12. In the example shown in FIG.

13, an intracerebral bleeding group is set to red-hatching, an LVO group is set to blue-hatching, and an infarction group is set to green-hatching, respectively, as a display aspect.

The number of abnormal signal regions and the positions of the abnormal signal regions of the tomographic image 32A shown in second display control are the same as those of the abnormal signal regions of the tomographic image 32A illustrated in the first display control. In the second display control, "H1" in the left hemisphere is classified into the intracerebral bleeding group, and is thus red-hatched (shown by a dotted line quadrangle). "H2" in the left hemisphere likewise is classified into the LVO group, and is thus blue-hatched (shown by a dotted line triangle). The intracerebral bleeding group and the LVO group are a high signal group into which the high signal region H is classi-fied. The infarction group is a low signal group into which the low signal region L is classified. The two low signal regions L of "L1" and "L2" are classified into the infarction group and are green-hatched. In this way, in the second display control, the display aspect of the abnormal signal region is changed depending on the classification reflecting a user's intention.

As described above, the medical support device 11 executes the first display control for displaying the abnormal signal regions detected by performing the image analysis on the medical image for which the tomographic image 32A is shown as an example, in an identifiable manner and the second display control for changing the display aspect for each group classified by the operation instruction, on the abnormal signal regions. For this reason, since the second display control can be executed in addition to the first display control, the convenience for the user is improved compared to the related art.

More specific description will be provided as follows. The second display control depending on the classification of the user is combined in addition to the first display control, whereby it is possible to execute a display method of displaying the abnormal signal regions as the analysis result of the image analysis in an identifiable manner and a display method of displaying the abnormal signal regions in the display aspects depending on the classification of the user, and it is possible to confirm the abnormal signal regions from a plurality of viewpoints. For this reason, diagnosis from a plurality of viewpoints is easily performed, and the convenience for the user is improved. The second display control is executed, whereby it is possible to change the display aspect while collecting a plurality of abnormal signal regions classified by the user into each group. While labeling for individually attaching annotation to the abnormal signal regions is heretofore performed, batch display control can be executed for each group, so that the classification of the abnormal signal regions is easily performed, and the con-venience for the user is improved.

In the present example, the processor 41 classifies the abnormal signal regions into at least two signal regions of a high signal region as an example of a first abnormal signal region and a low signal region as an example of a second abnormal signal region depending on the signal value and changes the display aspect between the classified first abnor-mal signal region and second abnormal signal region, in the first display control. With this, it is effective for diagnosis of an injury and a disease where both the first abnormal signal region and the second abnormal signal region that change depending on the signal value are found.

In the present example, the first abnormal signal region is the high signal region H where the signal value is relatively high, and the second abnormal signal region is the low signal region L where the signal value is relatively low. With this, for example, it is effective for diagnosis of an injury and a disease where both the high signal region H, such as intracerebral bleeding and LVO, and the low signal region L, such as infarction, are found. An example of an injury and a disease where both the high signal region H and the low signal region L are found is a stroke.

In the present example, the processor 41 displays the image display screen 70 as an example of an operation screen including the first list 51 that displays all the abnor-mal signal regions detected by the image analysis and the second list 85 that is generated for each group and is able to display the abnormal signal regions classified into each group. Then, the processor 41 receives the operation instruc-tion to classify the abnormal signal regions displayed in the first list 51 into the group through the image display screen 70 as an example of an operation screen and displays the abnormal signal regions classified into the group in the second list 85. With this, since it is possible to confirm a result of change by the operation instruction through the first list 51 and the second list 85, it is possible to easily ascertain a result of classification by the second display control compared to a case where a list is not displayed.

As described in the present example, the abnormal signal region in one of the first list 51 or the second list 85 is designated and dragged and dropped onto the other list, whereby the group to which the abnormal signal region belongs can be changed. With this, since the operation instruction to classify the abnormal signal regions can be given through the first list 51 and the second list 85, an intuitive operation can be performed compared to a case where a list is not used.

The operation instruction to classify the abnormal signal regions is not limited thereto, and for example, the following method may be employed. That is, in a case where one abnormal signal region in the first list 51 is selected by the pointer 73 or the like, the processor 41 presents a group list including a plurality of groups to be candidates of the second list 85 into which the selected abnormal signal region can be classified. In a case where designation of one group in the presented group list is received, the processor 41 classifies the abnormal signal region designated in the first list 51 into the second list 52 of the designated group.

In the present example, the user can optionally set the groups of the second list 85, and the processor 41 displays the second list 85 for each group. Since the user can optionally set the groups, it is possible to perform grouping reflecting a user's intention.

The group of the second list 85 can be set for each finding of the abnormal signal region, and the processor 41 displays the name of the finding as the group name of the second list 85. With this, since it is possible to perform grouping of each finding, it is possible to ascertain the abnormal signal regions for each finding. In a case of setting the group for each finding of the abnormal signal region, the group may be automatically set based on a use history of a finding used in image diagnosis by the user or a group to which the user belongs, in the past. The use history of the finding includes the presence or absence of use of the finding, a use frequency of the finding, a use rate, and the like. The group to which the user belongs indicates, for example, a group having the same information regarding a treatment department or a medical facility to which the user belongs. Candidates of finding information set based on the use history of the findings of the user in the past may be presented, and a finding may be set as the group of the second list 85 depending on user's selection from among the candidates.

In the present example, the tomographic image 32A shown as an example of a medical image is a brain image in which a brain is rendered, and as shown in FIG. 12 and the like, the findings include any of "infarction", bleeding, LVO, Hyperdense sign, and calcification. Such findings are findings that are often observed in a stroke, and in a case where the group of each finding is set as the group of the second list 85, it is effective for diagnosis of a stroke.

Second Embodiment

Figure 14:
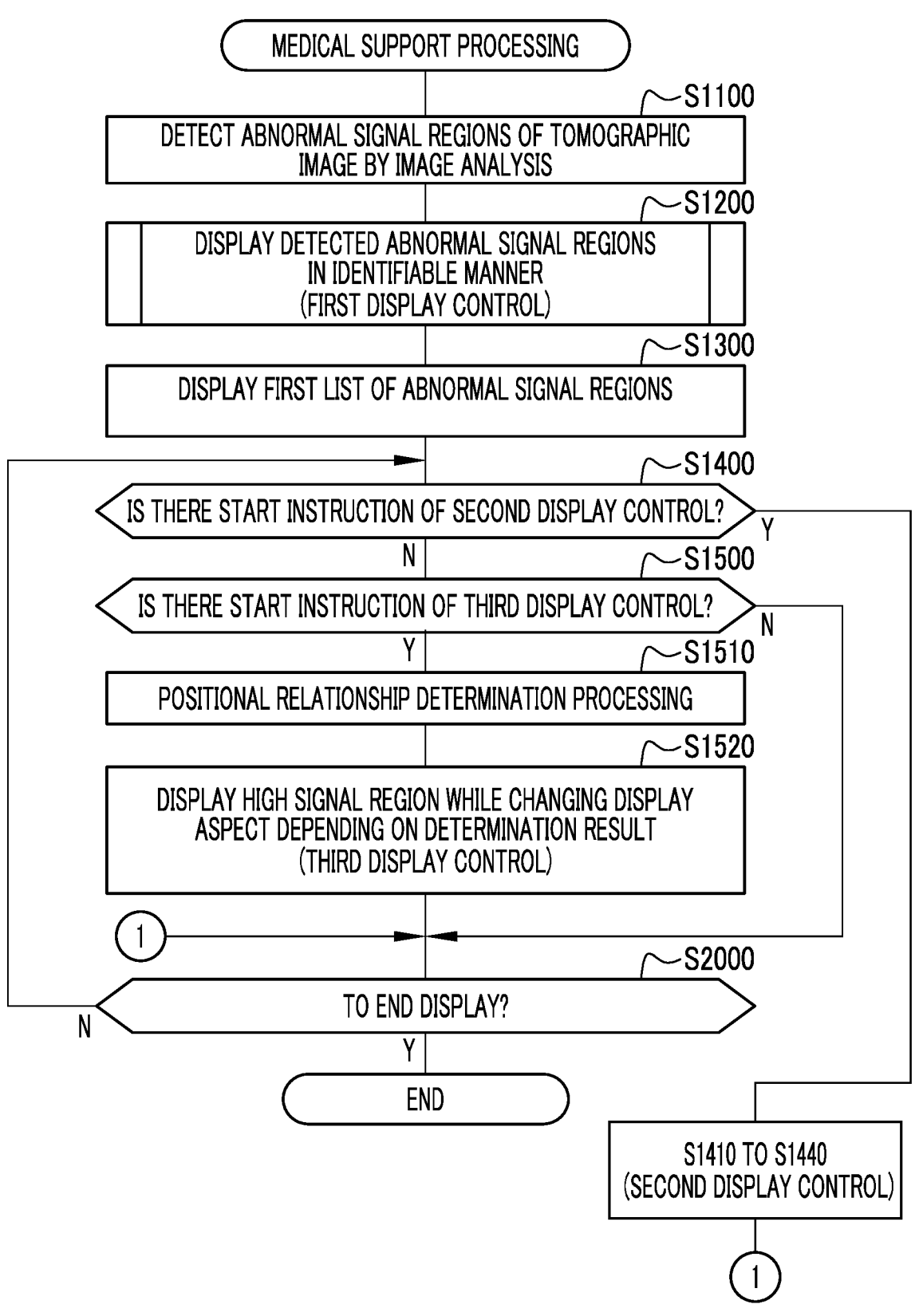
FIG. 14 is a flowchart showing a processing procedure of medical support processing of a second embodiment.

A second embodiment shown in FIGS. 14 and 15 is an example where the processor 41 further executes third display control in addition to the first display control and the second display control. The third display control is display control for determining, in a case where there are a first abnormal signal region and a second abnormal signal region classified depending on the signal value in a plurality of abnormal signal regions, whether or not the first abnormal signal region has a positional relationship set in advance with respect to the second abnormal signal region, and changing the display aspect of the first abnormal signal region depending on a determination result. For example, the processor 41 changes a display aspect of a high signal region H as an example of the first abnormal signal region depending on a positional relationship with a low signal region L as an example of the second abnormal signal region. Hereinafter, the third display control will be described with this case as an example.

A flowchart shown in FIG. 14 is a flowchart illustrating a procedure of medical support processing of the second embodiment. Process of Steps S1100 to S1300 is the same as in the flowchart of the first embodiment shown in FIG. 3, and thus, description will not be repeated. Processing regarding the second display control of Steps S1400 to S1440 is briefly shown in FIG. 14. In Step S1400, in a case where the start instruction of the second display control is not input (in Step S1400, N), the processor 41 proceeds to Step S1500.

In Step S1500, the processor 41 waits for an input of a start instruction of the third display control from the user. In a case where the start instruction of the third display control is input, the processor 41 proceeds to Step S1510, and executes positional relationship determination processing on the high signal region H detected in the tomographic image 32A. Then, in Step S1520, the processor 41 executes the third display control for displaying the high signal region H while changing the display aspect depending on a determination result.

FIG. 15 is a diagram schematically showing the third display control. In the third display control, the display aspect of the abnormal signal region is changed following a third display rule. According to the third display rule of FIG. 15, in a case where the high signal region H has no positional relationship (hereinafter, referred to as a predetermined positional relationship) set in advance with the low signal region L, the high signal region H determined to have no positional relationship is classified into a high signal group 1. On the other hand, in a case where the high signal region H has the predetermined positional relationship with the low signal region L, the high signal region H determined to have the predetermined positional relationship is classified into a high signal group 2. In the present example, the presence or absence of the predetermined positional relationship is presence or absence of the high signal region H and the low signal region L in the same hemisphere as a brain, in a brain image. A right hemisphere and a left hemisphere are an example of anatomical regions of the brain. That is, the presence or absence of the positional relationship is an example of the presence or absence of the first abnormal signal region and the second abnormal signal region in the same anatomical region in the brain as an example of an organ rendered in the tomographic image 32A.

In the tomographic image 32A of the present example, two low signal regions L of "L1" and "L2" are present in the right hemisphere, and are not present in the left hemisphere. On the other hand, two high signal regions H of "H1" and "H2" are present in the left hemisphere, and one high signal region H of "H3" is present in the right hemisphere. Accordingly, the high signal region H having the predetermined positional relationship with the low signal region L is "H3". The processor 41 determines an anatomical region of an organ by image analysis using the machine learning model that performs semantic segmentation described above, as an example. The processor 41 executes the positional relationship determination processing by performing the determination of the anatomical region and the detection of the abnormal signal regions.

In the third display rule of the present example, red-hatching is set as the display aspect of the high signal group 1 having no the predetermined positional relationship with the low signal region L, and blue-hatching is set as the display aspect of the high signal group 2 having the predetermined positional relationship with the low signal region L. For this reason, in the tomographic image 32A, the two high signal regions H of "H1" and "H2" present in the left hemisphere are red-hatched (in FIG. 15, shown by a dotted line quadrangle), and the high signal region H of "H3" present in the right hemisphere is blue-hatched (in FIG. 15, shown by a dotted line triangle). In the present example, the low signal regions L of "L1" and "L2" classified into the infarction group are green-hatched (in FIG. 15, shown by a dotted line rhombus).

In this way, in the third display control, like "H3", even in a case of the same high signal region H as "H1" and "H2", the display aspect is changed depending on the determination result regarding whether or not to have the positional relationship set in advance with respect to the low signal region L. In a case of a stroke, as shown in the present example, the presence of both the high signal region H and the low signal region L in the same hemisphere is an important index in diagnosis. For this reason, the third display control is effective for diagnosis of an injury and a disease where the presence of the first abnormal signal region and the second abnormal signal region having different signal values, such as the high signal region H and the low signal region L, in the same anatomical region is an important index.

In the above-described example, although the high signal region H has been described as the first abnormal signal region as an example, the first abnormal signal region may be the low signal region L. That is, determination may be made whether or not the low signal region L has the predetermined positional relationship with the high signal region H, and the display aspect of the low signal region L may be changed depending on a determination result.

In the above-described example, although the presence or absence of the first abnormal signal region and the second abnormal signal region in the same anatomical region of the organ has been described as an example of the presence or absence of the predetermined positional relationship, the positional relationship may be other relationships. For example, the presence or absence of the first abnormal signal region and the second abnormal signal region at a distance set in advance may be employed.

Figure 16:
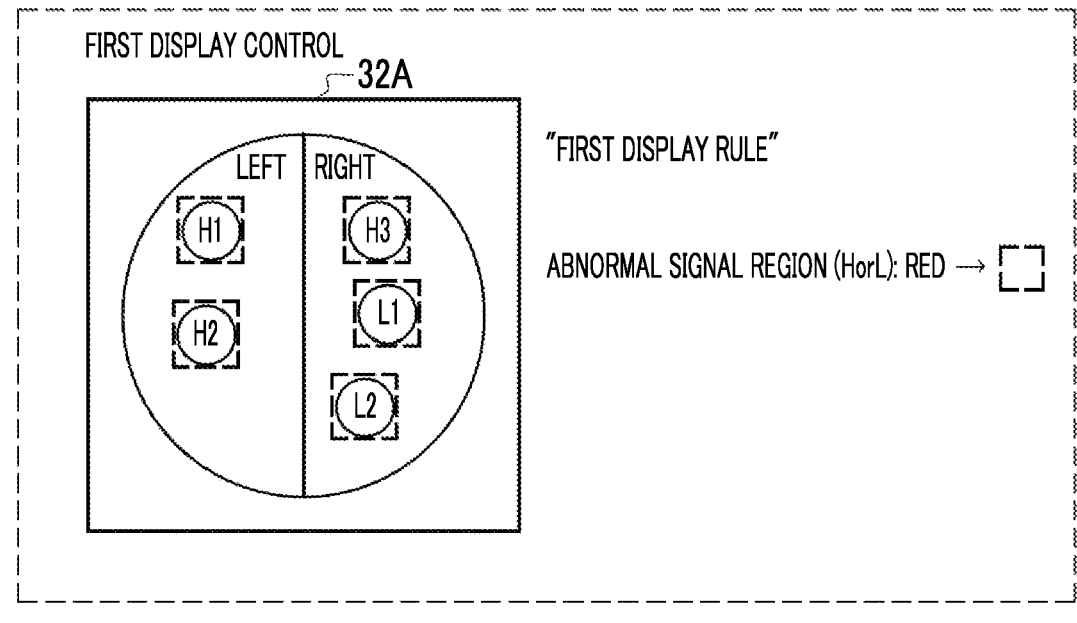
FIG. 16 is a diagram showing a modification example of first display control.

In the above-described example, although an example where the display aspects of the first abnormal signal region (as an example, the high signal region H) and the second abnormal signal region (as an example, the low signal region L) having different signal value are changed in the first display control has been described, as shown in FIG. 16, the display aspects of the first abnormal signal region and the second abnormal signal region may not be changed. In FIG. 16, the high signal region H and the low signal region L are not distinguished and are red-hatched as the abnormal signal regions (in FIG. 16, shown by a dotted line quadrangle). That is, in the first display control, the abnormal signal regions detected by the image analysis may be displayed in the medical image in an identifiable manner, and the display aspect may not be changed depending on whether the abnormal signal region is the high signal region or the low signal region.

The third display control shown in FIG. 15 can also be said as an example of the first display control since the abnormal signal regions are displayed in the medical image in an identifiable manner. For this reason, as shown in FIG. 17, the processor 41 may execute the second display control for changing the display aspect for each group classified by the operation instruction, and the third display control as an example of the first display control. This means that the first display control shown in FIGS. 13 and 15 is not executed, and the third display control is executed as an example of the first display control, instead of the first display control. A combination example of the second display control and the third display control is as follows. For example, in a case where the ANALYZE button 72 of the image display screen 70 is operated, the processor 41 executes the image analysis, and executes the third display control based on the detected abnormal signal region. Thereafter, the processor 41 executes the second display control based on the group designation of the user.

The three kinds of display control of the first display control, the second display control, and the third display control may be selectively executed. As shown in FIGS. 3 and 14, although the second display control or the third display control is executed after the first display control, the order of the display control is not limited thereto, and may be a reverse order. In the example of FIG. 14, although the third display control is executed in addition to the first display control and the second display control, the third display control may be executed instead of the second display control.

Figure 18:
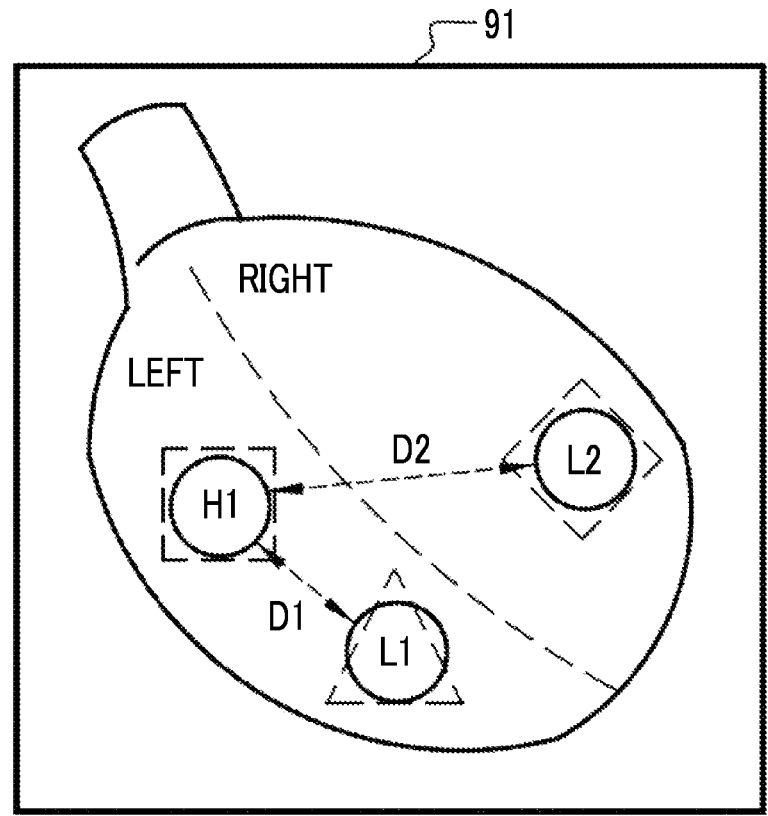
FIG. 18 is a diagram showing a cardiac image.

In the above-described example, although the brain image in which the brain is rendered as an organ has been shown as an example of a medical image, of course, the medical image may be images other than the brain image. For example, as shown in FIG. 18, a cardiac image 91 in which a heart is rendered as an organ may be employed. Even in the cardiac image 91, not only the first display control and the second display control, but also the third display control can be executed. The heart has anatomical regions of, for example, a right atrium and a left atrium. For this reason, even in the cardiac image 91, in a case where "H1" of a high signal region H and "L1" of a low signal region L are present in the same anatomical region, the display aspect may be changed with respect to a case where the high signal region H and the low signal region L are present in different anatomical regions. In regard to "L1" and "L2" of low signal regions L, the display aspect may be changed depending on distances D1 and D2 from "H1" of the high signal region H.

A determination region for determining whether or not the high signal region H and the low signal region L is not limited to the anatomical region. The determination region may be, for example, a region in the heart divided using Voronoi tessellation with a blood vessel as a fixed point or a fixed line.

In the above-described example, although the tomography apparatus has been described as a modality that captures the medical image as an example, the modality is not limited to the tomography apparatus, and may be a modality, such as an X-ray imaging apparatus that captures a simple X-ray image, a mammography, an endoscope, and an ultrasound diagnostic apparatus.

In the above-described embodiment, for example, as a hardware structure of processing units that execute various kinds of processing, such as the image analysis unit and the display control unit, various processors described below can be used. Various processors include a programmable logic device (PLD) that is capable of changing a circuit configuration after manufacturing, such as a field-programmable gate array (FPGA), and a dedicated electric circuit that is a processor having a circuit configuration dedicatedly designed for executing specific processing, such as an application specific integrated circuit (ASIC), in addition to a CPU that is a general-purpose processor configured to execute software (program) to function as various processing units.

Various kinds of processing described above may be executed by one of various processors or may be executed by a combination of two or more processors (for example, a combination of a plurality of FPGAs or a CPU and an FPGA) of the same type or different types. A plurality of processing units may be configured with one processor. As an example where a plurality of processing units are configured with one processor, like system on chip (SOC), there is a form in which a processor that realizes all functions of a system including a plurality of processing units into one integrated circuit (IC) chip is used.

In this way, various processing units are configured using one or more processors among various processors described above as a hardware structure.

In addition, as the hardware structure of various processors, more specifically, an electric circuit (circuitry), in which circuit elements, such as semiconductor elements, are combined can be used.

In addition to the operation program of a medical support device, the technique of the present disclosure extends to a computer readable storage medium (a USB memory or a digital versatile disc (DVD)-read only memory (ROM), or the like) that stores the operation program of a medical support device in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All cited documents, patent applications, and technical standards described in the specification are incorporated by reference in the specification to the same extent as in a case where each individual cited document, patent application, or technical standard is specifically and individually indicated to be incorporated by reference.

What is claimed is:

1. A medical support device comprising:

a processor, wherein the processor is configured to:

execute first display control for displaying abnormal signal regions detected by performing image analysis on a medical image, in an identifiable manner;

display an operation screen including a first list that displays all of the abnormal signal regions detected by the image analysis and a second list that is generated for each group into which the abnormal signal regions are classified;

receive an operation instruction to classify the abnormal signal regions displayed in the first list into the group through the operation screen; and execute second display control for changing a display aspect for each group classified by the operation instruction, on the abnormal signal regions.

2. The medical support device according to claim 1, wherein the processor is configured to:

classify the abnormal signal regions into at least two regions of a first abnormal signal region and a second abnormal signal region depending on a signal value and change the display aspect between the classified first abnormal signal region and second abnormal signal region, in the first display control.

3. The medical support device according to claim 2, wherein the first abnormal signal region is a high signal region where the signal value is relatively high, and the second abnormal signal region is a low signal region where the signal value is relatively low.

4. The medical support device according to claim 1, wherein the processor is configured to:

display the abnormal signal regions classified into the group in the second list.

5. The medical support device according to claim 4, wherein the group is able to be optionally set by a user, and the processor is configured to display the second list for each group.

6. The medical support device according to claim 5, wherein the group is able to be set for each finding of the abnormal signal region, and the processor is configured to display a name of the finding as a group name of the second list.

7. The medical support device according to claim 6, wherein the medical image is a brain image in which a brain is rendered, and

the finding includes any of infarction, bleeding, LVO, Hyperdense sign, and calcification in the brain.

8. The medical support device according to claim 1, wherein the processor is configured to:

in a case where there are a first abnormal signal region and a second abnormal signal region classified depending on a signal value in a plurality of the abnormal signal regions;

determine whether or not the first abnormal signal region has a positional relationship set in advance with respect to the second abnormal signal region; and execute third display control for changing a display aspect of the first abnormal signal region depending on a determination result of the positional relationship.

9. The medical support device according to claim 8, wherein the first abnormal signal region is a high signal region where the signal value is relatively high, and the second abnormal signal region is a low signal region where the signal value is relatively low.

10. The medical support device according to claim 8, wherein presence or absence of the positional relationship is presence or absence of the first abnormal signal region and the second abnormal signal region in the same anatomical region of an organ rendered in the medical image.

11. An operation method of a medical support device including a processor, the operation method comprising:

executing, by the processor, first display control for displaying abnormal signal regions detected by performing image analysis on a medical image, in an identifiable manner;

displaying an operation screen including a first list that displays all of the abnormal signal regions detected by the image analysis and a second list that is generated for each group into which the abnormal signal regions are classified;

receiving an operation instruction to classify the abnormal signal regions displayed in the first list into the group through the operation screen; and executing second display control for changing a display aspect for each group classified by the operation instruction, on the abnormal signal regions.

12. A non-transitory computer-readable storage medium storing an operation program of a medical support device that causes a computer to function as a medical support device, the operation program causing the computer to execute:

first display control for displaying abnormal signal regions detected by performing image analysis on a medical image, in an identifiable manner;

displaying an operation screen including a first list that displays all of the abnormal signal regions detected by the image analysis and a second list that is generated for each group into which the abnormal signal regions are classified;

receiving an operation instruction to classify the abnormal signal regions displayed in the first list into the group through the operation screen; and second display control for changing a display aspect for each group classified by the operation instruction, on the abnormal signal regions.

* * * * *